(12) United States Patent
Lopez et al.

(10) Patent No.: US 9,956,300 B2
(45) Date of Patent: May 1, 2018

(54) HYDROGELS FORMED FROM POLYPEPTIDE MICELLES AND METHODS OF USE THEREOF

(71) Applicant: Duke University, Durham, NC (US)

(72) Inventors: Gabriel P. Lopez, Durham, NC (US); Ashutosh Chilkoti, Durham, NC (US); Ali Ghoorchian, Durham, NC (US); Joseph R. Simon, Durham, NC (US)

(73) Assignee: Duke Univerity, Durham, NC (US)

( * ) Notice: Subject to any disclaimer, the term of this patent is extended or adjusted under 35 U.S.C. 154(b) by 0 days. days.

(21) Appl. No.: 15/074,132

(22) Filed: Mar. 18, 2016

(65) Prior Publication Data
US 2016/0271262 A1 Sep. 22, 2016

Related U.S. Application Data

(60) Provisional application No. 62/134,672, filed on Mar. 18, 2015.

(51) Int. Cl.
| | |
|---|---|
| *A61K 47/00* | (2006.01) |
| *C07K 14/00* | (2006.01) |
| *A61K 47/48* | (2006.01) |
| *A61K 9/06* | (2006.01) |
| *C08J 3/075* | (2006.01) |
| *A61L 27/22* | (2006.01) |
| *A61L 27/52* | (2006.01) |
| *C07K 14/78* | (2006.01) |
| *A61K 47/64* | (2017.01) |
| *A61K 47/69* | (2017.01) |

(52) U.S. Cl.
CPC .............. *A61K 47/488* (2013.01); *A61K 9/06* (2013.01); *A61K 47/64* (2017.08); *A61K 47/6907* (2017.08); *A61L 27/227* (2013.01); *A61L 27/52* (2013.01); *C07K 14/78* (2013.01); *C08J 3/075* (2013.01); *A61L 2300/252* (2013.01); *A61L 2300/626* (2013.01)

(58) Field of Classification Search
None
See application file for complete search history.

(56) References Cited

U.S. PATENT DOCUMENTS

2006/0240092 A1* 10/2006 Breitenkamp ....... A61K 9/1075 424/450

OTHER PUBLICATIONS

Hassouneh et al. Biomacromolecules 2013, 14, 2347-2353.*
Jhaveri et al., Frontiers in Pharmacology, Apr. 2014, vol. 5, Article 77.*
Hoare et al. Polymer 49 (2008) 1993-2007.*
J. Herbert Waite et al.: "The Peculiar Cottagens of Mussel. Byssus", Matrix Biology, 1998, vol. 17, pp. 93-106.
Dan E. Meyer et al.: "Quantification of the Effects of Chain Length and Concentration on the Thermal Behavior of Elastin-like Polypeptides", Biomacromolecules, 2004, vol. 5, pp. 846-851.
Ali Ghoorchian et al.: "Molecular Architecture Influences the Thermally InducedAggregation Behavior of Elastin-like Polypeptides", Biomacromolecules, 2011, vol. 12, pp. 4022-4029.
D. W. Urry et al.: "Phase-Structure Transitions of the Elastin Polypentapeptide-Water System Within the Framework of Composition-Temperature Studies", Biopolymers, 1985, vol. 24, pp. 2345-2356.
Dan E. Meyer et al.: "Genetically Encoded Synthesis of Protein-Based Polymers with Precisely Specified Molecular Weight and Sequence by Recursive Directional Ligation: Examples from the Elastin-like Polypeptide System", Biomacromolecules, 2002, vol. 3, pp. 357-367.
Younhee Cho et al.: "Effects of Hofmeister Anions on the Phase Transition Temperature of Elastin-like Polypeptides", J Phys Chem B., Nov. 6, 2008, vol. 112, No. 44, pp. 13765-13771.
Dan E. Meyer et al.: "Purification of recombinant proteins by fusion with thermally-responsive polypeptides", Nature Biotechnology, Nov. 1999, vol. 17, pp. 1112-1115.
David T. McPherson et al.: "Production and Purification of a Recombinant Elastomeric Polypeptide, G-(VPGVG)IS-VPGV, from *Escherichia coli*", Biotechnol. Prog, 1992, vol. 8, pp. 347-352.
Matthew R. Dreher et al.: "Temperature Triggered Self-Assembly of Polypeptides into Multivalent Spherical Micelles", J Am Chem Soc. Jan. 16, 2008, vol. 130, No. 2, pp. 687-694.
Jonathan R. McDaniel et al.: "Rational Design of "Heat Seeking"Drug Loaded Polypeptide Nanoparticles That Thermally Target Solid Tumors", NanoLett. 2014, vol. 14, pp. 2890-2895.
Daniel J. Callahan et al.: "Triple stimulus-responsive polypeptide nanoparticles that enhance intratumoral spatial distribution", Nano Lett., Apr. 11, 2012, vol. 12, No. 4, pp. 2165-2170.
Andrew J. Simnick et al.: "In vivo tumor targeting by a NGR decorated micelle of a recombinant diblock copolypeptide", J Control Release., Oct. 30, 2011, vol. 155, No. 2, pp. 144-151.
Wafa Hassouneh et al.: "Unexpected multivalent display of proteins by temperature triggered self-assembly of elastin-like polypeptide blockcopolymers", Biomacromolecules, May 14, 2012, vol. 13, No. 5, pp. 1598-1605.
Elin Hadler-Olsen et al.: "Regulation of matrix metalloproteinase activity in health and disease", FEBS Journal, 2011, vol. 278, pp. 28-45.
Wolfram Bode et al.: "Astacins, serralysins, snake venom and matrix metalloproteinases exhibit identical zinc-binding environments (HEXXHXXGXXH and Met-turn) and topologies and should be grouped into a common family, the 'metzincins'", Federation of European Biochemical Societies, Sep. 1993, vol. 331, No. 1,2, pp. 134-140.
K. Kasperek et al.: "Serum Zinc Concentration during Childhood", Europ. J. Pediat., 1977, vol. 126, pp. 199-202.

(Continued)

*Primary Examiner* — Jeanette M Lieb
(74) *Attorney, Agent, or Firm* — NK Patent Law, PLLC

(57) ABSTRACT

The presently disclosed subject matter is directed to compositions, methods, and systems (e.g., platforms) comprising the same, the systems comprising, consisting of, or consisting essentially of micro- and macro-hydrogels that are formed from polypeptide micelles. The systems have enhanced mechanical properties that can be useful in a wide variety of applications, can be used for controlled release of drug-loaded micelles, and can be designed to reversibly assemble and disassemble on demand.

20 Claims, 19 Drawing Sheets

(56) References Cited

OTHER PUBLICATIONS

Paula Trumbo et al.: "Dietary Reference Intakes : Vitamin A, Vitamin K, Arsenic, Boron, Chromium, Copper, Iodine, Iron, Manganese, Molybdenum, Nickel, Silicon, Vanadium and Zinc", J. Am. Diet. Assoc., 2001, vol. 101, pp. 294-300.
Jens Danielsson et al.: "Translational diffusion measured by PFG-NMR on full length and fragments of the Alzheimer Abeta(1-40) peptide. Determination of hydrodynamic radii of random coil peptides of varying length", Magnetic Resonance in Chemistry, 2002, vol. 40, pp. S89-S97.
Ali Ghoorchian et al.: "Size and Shape Characterization of Thermo reversible Micelles of Three-Armed Star Elastin-Like Polypeptides", J.Phys.Chem.B, 2013, vol. 117, pp. 8865-8874.
Ali Ghoorchian et al.: "Thermoreversible Micelle Formation Using a Three-Armed Star Elastin-like Polypeptide", Macromolecules, 2010, vol. 43, pp. 4340-4345.
Jonathan R. McDaniel et al.: "Self-Assembly of Thermally Responsive Nanoparticles of a Genetically Encoded Peptide Polymer by Drug Conjugation", Chemie-International Edition, 2013, vol. 52, pp. 1683-1687.
H. Kumari et al.: "Aqueous solubilization of hydrophobic supramolecular metal-organic nanocapsules", Chem. Sci., 2014, vol. 5, pp. 2554-2559.
Bhuvnesh Bharti et al.: "Aggregation of Silica Nanoparticles Directed by Adsorptionof Lysozyme", Langmuir, 2011, vol. 27, pp. 9823-9833.
Jan Skov Pedersen et al.: "A Small-Angle Neutron and X-ray Contrast Variation Scattering Study of the Structure of Block Copolymer Micelles: Corona Shape and Excluded Volume Interactions", Macromolecules, 2003, vol. 36, pp. 416-433.
S. Chandrasekhar: "Stochasti Problems in Physics and Astronomy", Reviews of Modern Physics, Jan. 1943, vol. 15, No. 1.
Kyung Jae Jeong et al.: "Interplay between Covalent and Physical Interactions within Environment Sensitive Hydrogels", Biomacromolecules, 2009, vol. 10, pp. 1090-1099.
Congqi Yan et al.: "Rheological properties of peptide-based hydrogels for biomedical and other applications", Chem Soc Rev., Sep. 2010, vol. 39, No. 9, pp. 3528-3540.
Judith T. Cirulis et al.: "Viscoelastic properties and gelation of an elastin-like polypeptide", Journal of Rheology, 2009, vol. 53, No. 5, pp. 1215-1228.
Daisuke Asai et al.: "Protein polymer hydrogels by in situ,rapid and reversible self gelation", Biomaterials, 2012, vol. 33, Issue 21, pp. 5451-5458.
Donghua Xu et al.: "Rheological Properties of Cysteine-Containing Elastin-Like Polypeptide Solutions and Hydrogels", Biomacromolecules, 2012, vol. 13, pp. 2315-2321.
Daniel G. Abebe et al.: "Controlled Thermo responsive Hydrogels by Stereo complexed PLA-PEG-PLA Prepared via Hybrid Micelles of Pre-Mixed Copolymers with Different PEG Lengths", Biomacromolecules, 2012, vol. 13, pp. 1828-1836.
Victor Breedveld et al.: "Rheology of Block Copolypeptide Solutions: Hydrogels with Tunable Properties", Macromolecules, 2004, vol. 37, pp. 3943-3953.
Tsuguyuki Saito et al.: "Self-aligned integration of native cellulose nanofibrils towards producing diverse bulk materials", Soft Matter, 2011, vol. 7, pp. 8804-8809.
C. R. Rubinstein M, Polymer Physics, Oxford University Press, 2012.
Lennart H. Beun et al.: "From Micelles to Fibers: Balancing Self-Assembling and Random Coiling Domains in pH-Responsive Silk-Collagen-Like Protein-Based Polymers", Biomacromolecules, 2014, vol. 15, pp. 3349-3357.
Devin G. Barrett et al.: "pH-Based Regulation of Hydrogel Mechanical Properties Through Mussel-Inspired Chemistry and Processing", Advanced Functional Materials, 2013, vol. 23, pp. 1111-1119.
Dominic E. Fullenkamp et al.: "Mussel-Inspired Histidine-Based Transient Network Metal Coordination Hydrogels", Macromolecules, 2013, vol. 46, pp. 1167-1174.
Murat Guvendiren et al.: "Shear-thinning hydrogels for biomedical applications", Soft Matter, 2012, vol. 8, pp. 260-272.
Niels Holten-Andersen et al.: "pH-induced metal-ligand cross-links inspired by mussel yield self-healing polymer networks with near-covalent elastic moduli", Proc. Natl. Acad. Sci. U. S. A., 2011, vol. 108, No. 7, pp. 2651-2655.
Vlasaki Nakahata et al.: "Redox-responsive self-healing materials formed from host-guest polymers", 2011, vol. 2:511.
Maartje M. C. Bastings et al.: "A Fast pH-Switchable and Self-Healing Supramolecular Hydrogel Carrier for Guided, Local Catheter Injection in the Infarcted Myocardium", Adv. Healthcare Mater., 2014, vol. 3, pp. 70-78.
Jonathan R. McDaniel et al.: "Recursive Directional Ligation by Plasmid Reconstruction Allows Rapid and Seamless Cloning of Oligomeric Genes", Biomacromolecules, 2010, vol. 11, pp. 944-952.
Wafa Hassouneh et al.: "Fusions of elastin-like polypeptides to pharmaceutical proteins", Methods Enzymol., 2012, vol. 502, pp. 215-237.
Chung C et al.: "Tetrakis(hydroxymethyl) phosphonium chloride as a covalent cross-linking agent for cell encapsulation within protein-based hydrogels.", Biomacromolecules, Dec. 10, 2012, vol. 13, No. 12, pp. 3912-3916.
Jonathan R. McDaniel et al.: "Roadmap for the design of drug-loaded thermo responsive polypeptide nanoparticles", Angew Chem Int Ed Engl., Feb. 4, 2013, vol. 52, No. 6, pp. 1683-1687.
Andrew L. Lewis et al.: "DC Bead: In Vitro Characterization of aDrug-delivery Device for TransarterialChemoembolization", Journal of vascular and interventional radiology, 2006, vol. 17, No. 2, pp. 335-342.
Jordi Bruix et al.: "Management of Hepatocellular Carcinoma", Hepatology, 2005, vol. 42, No. 5, pp. 1208-1236.
Johannes Lammer et al.: "Prospective Randomized Study of Doxorubicin-Eluting-Bead Embolization in the Treatment Df Hepatocellular Carcinoma:Results of the Precision V Study", Cardiovascular and Interventional Radiology, 2010, vol. 33, pp. 41-52.
Maria Varela et al.: "Chemoembolization of hepatocellular carcinoma with drugeluting beads: Efficacy and doxorubicin pharmacokinetics", Journal of Hepatology, 2007, vol. 46, pp. 474-481.
Calogero Camma' et al.: "Transarterial Chemoembolization for Unresectable Hepatocellular Carcinoma: Meta-Analysis of Randomized ControlledTrials", Radiology, 2002, vol. 224, pp. 47-54.
Julien Namur et al.: "Drug-eluting Beads for Liver Embolization:Concentration of Doxorubicin in Tissue and inBeads in a Pig Model", Journal of Vascular and Interventional Radiology, 2010, vol. 21, pp. 259-267.
J. Andrew MacKay et al.: "Self-assembling chimeric polypeptide-doxorubicin conjugate nanoparticles that abolish tumors after a single injection", Nature materials, 2009, vol. 8, No. 12, pp. 993-999.
Ryusaku Yamada et al.: "Hepatic Artery Emolization in 120 patients with Unresectable Hepatoma", Radiology, Aug. 1983, vol. 148, pp. 397-401.
Simon M. Joscelyne et al.: "Membrane emulsification—a literature review", Journal of Membrane Science, 2000, vol. 169, pp. 107-117.
Eleanor F. Banwell et al.: "Rational design and application of responsive alpha-helical peptide hydrogels", Nature Materials, Jul. 2009, vol. 8, pp. 596-600.
Ohm D. Krishna et al.: "Protein- and Peptide-Modified Synthetic Polymeric Biomaterials", Biopolymers, 2010, vol. 94, No. 1, pp. 32-48.
Lewis A. Reis et al.: "A peptide-modified chitosan-collagen hydrogel for cardiac cell culture and delivery", Acta Biomaterialia, 2012, vol. 8, pp. 1022-1036.
Arne Skerra : "Engineered protein scaffolds for molecular recognition", Journal of Molecular Recognition, 2000, vol. 13, pp. 167-187.
Christopher G Tate et al.: "Engineering G protein-coupled receptors to facilitate their structure determination", Structural Biology, 2009, vol. 19, pp. 386-395.

(56) References Cited

OTHER PUBLICATIONS

Naresh Chennamsetty et al.: "Design of therapeutic proteins with enhanced stability", Proceedings of the National Academy of Sciences, Jul. 21, 2009, vol. 106, No. 29, pp. 11937-11942.
Brandon V. Slaughter et al.: "Hydrogels in Regenerative Medicine", Adv Mater., Sep. 4, 2009, vol. 21, No. 0, pp. 3307-3329.
John R. Luther et al.: "Genetically Engineered Charge Modifications to Enhance Protein Separation in Aqueous Two-Phase Systems: Electrochemical Partitioning", Biotechnology and Bioengineering, 1994, vol. 44, pp. 147-153.
Ricardo Capone et al.: "Designing Nanosensors Based on Charged Derivatives of Gramicidin A", Journal of the American Chemical Society (ACS Publications), 2007, vol. 129, pp. 9737-9745.
Andreas Hennig et al.: "Stimuli-Responsive Polyguanidino-Oxanorbornene Membrane Transporters as Multicomponent Sensors in Complex Matrices", Journal of the American Chemical Society (ACS Publications), 2008, vol. 130, pp. 10338-10344.
Scott Banta et al.: "Protein Engineering in the Development of Functional Hydrogels", Annu. Rev. Biomed. Eng., 2010, vol. 12, pp. 167-186.
Cheryl T. S. Wong Po Foo et al.: "Two-component protein-engineered physical hydrogels for cell encapsulation", Proceedings of the National Academy of Sciences, Dec. 29, 2009, vol. 106, No. 522, pp. 2067-22072.
W.E. Hennink et al.: "Novel crosslinking methods to design hydrogels", Advanced Drug Delivery Reviews, 2012, vol. 64, pp. 223-236.
J. Berger et al.: "Structure and interactions in covalently and ionically crosslinked chitosan hydrogels for biomedical applications", European Journal of Pharmaceutics and Biopharmaceutics, 2004, vol. 57, pp. 19-34.
Garret D. Nicodemus et al.: "Cell Encapsulation in Biodegradable Hydrogels for Tissue Engineering Applications", Tissue Engineering: Part B, 2008, vol. 14, No. 2, pp. 149-165.
W.E. Hennink et al.: "Novel crosslinking methods to design hydrogels", Advanced Drug Delivery Reviews, 2002, vol. 54, pp. 13-36.
Joshua A. Gustafson et al.: "Synthesis and Characterization of a Matrix-Metalloproteinase Responsive Silk-Elastinlike Protein Polymer", Biomacromolecules, 2013, vol. 14, pp. 618-625.
Draveen K. Sharma et al.: "The effect of pharmaceuticals on the nanoscale structure of PEO-PPO-PEO micelles", Colloids and Surfaces B: Biointerfaces 61 (2008), pp. 53-60.
Jeong-Yun Sun et al.: "Highly stretchable and tough hydrogels", Nature, Sep. 6, 2012, vol. 489, No. 7414, pp. 133-136.
Wei-Chun Lin et al.: "Large Strain and Fracture Properties of Poly(dimethylacrylamide)/SilicaHybrid Hydrogels", Macromolecules, 2010,vol. 43, pp. 2554-2563.
Sarvesh K. Agrawal et al.: "Nanoparticle-Reinforced Associative Network Hydrogels", Langmuir, Nov. 18, 2008, vol. 24, No. 22, pp. 13148-13154.
Deniz C. Tuncaboylu et al.: "Tough and Self-Healing Hydrogels Formed via HydrophobicInteractions", Macromolecules, 2011, vol. 44, pp. 4997-5005.
Jeremy Brassinne et al.: "Hydrogels with Dual Relaxation and Two-Step Gel-Sol Transition from Heterotelechelic Polymers", Macromolecules, 2013, vol. 46, pp. 9134-9143.

Matthew J. Glassman et al.: "Structure and Mechanical Response of Protein Hydrogels Reinforced by Block Copolymer Self-Assembly", Soft Matter, Aug. 7, 2013, vol. 9, No. 29, pp. 6814-6823.
Byeong-Su Kim et al.: "Hydrogen-Bonding Layer-by-Layer-Assembled Biodegradable Polymeric Micelles as Drug Delivery Vehicles from Surfaces", Acs Nano, 2008, vol. 2, No. 2, pp. 386-392.
Andre Laschewsky et al.: "Thermo-responsive Amphiphilic Di- and Triblock Copolymers Basedon Poly(N-isopropylacrylamide)and Poly(methoxy diethylene glycol acrylate):Aggregation and Hydrogel Formation in Bulk Solution and in Thin Films", Intelligent Hydrogels, Progress in Colloid and Polymer Science, 2013, vol. 140, pp. 15-34.
Lan Wei et al.: "Dual-drug delivery system based on hydrogel/micelle composites", Biomaterials, 2009, vol. 30, pp. 2606-2613.
Dong Ma et al.: "Novel supramolecular hydrogel/micelle composite for co-delivery of anticancer drug and growth factor", SoftMatter, 2012, vol. 8, pp. 3665-3672.
Pierre Guillet et al.: "Connecting micelles by metallo-supramolecular interactions: towards stimuli responsive hierarchical materials", Soft Matter, 2009, vol. 5, pp. 3409-3411.
Longxi Xiao et al.: "Mechano-responsive hydrogels crosslinked by block copolymer micelles", Soft Matter, 2012, vol. 8, pp. 10233-10237.
Bradley D. Olsen et al.: "Yielding Behavior in Injectable Hydrogels from Telechelic Proteins", Macromolecules, 2010, vol. 43, pp. 9094-9099.
Jeffrey D. Hartgerink et al.: "Self-Assembly and Mineralization of Peptide-Amphiphile Nanofibers", Science, Nov. 23, 2001, vol. 294, pp. 1684-1687.
Elizabeth R. Wright et al.: "Morphological Characterization of Elastin-Mimetic Block Copolymers Utilizing Cryo- and Cryoetch-HRSEM", Microsc. Microanal., 2003, vol. 9, pp. 171-182.
Marc André Meyers et al.: "Biological materials: Structure and mechanical properties", Progress in Materials Science, 2008, vol. 53, pp. 1-206.
Sabine Bechtle et al.: "On the mechanical properties of hierarchically structured biological materials", Biomaterials, 2010, vol. 31, pp. 6378-6385.
Michel Van Der Rest et al.: "Collagen family of proteins", The FASEB Journal, Oct. 1991, vol. 5, pp. 2814-2823.
Andrew J. Maniotis et al.:"Demonstration of mechanical connections between integrins,cytoskeletal filaments, and nucleoplasm that stabilize nuclear structure", Proc. Natl. Acad. Sci. USA, Feb. 1997, vol. 94, pp. 849-854.
Amy McGough et al.: "Cofilin Changes the Twist of F-Actin: Implications forActin Filament Dynamics and Cellular Function", The Journal of Cell Biology, Aug. 25, 1997, vol. 138, No. 4, pp. 771-781.
Naoko Mizuno et al.: "Three-dimensional structure of cytoplasmic dyneinbound to microtubules", The National Academy of Sciences of the USA, Dec. 26, 2007, vol. 104, No. 52, pp. 20832-20837.
Irina Massova et al.: "Matrix metalloproteinases: structures, evolution, and diversification", The FASEB Journal, Nov. 2016, vol. 12, No. 12 , pp. 1075-1095.
Frosty Loechel et al.: "Activation of ADAM 12 protease by copper", Federation of European Biochemical Societies, 2001, vol. 506, pp. 65-68.

\* cited by examiner

= MG-(VPGVG)$_{60}$(VPGAGVPGGG)$_{30}$HEDGHWDGSEHGY-G

— 5 min
20 min
— 40 min
1 hr
2 hr
3 hr
— 4 hr
5 hr
20 hr
24 hr
28 hr
90 hr
— 96 hr $\Delta c_1 > \Delta c_2 > \Delta c_3$

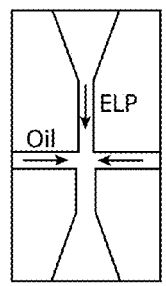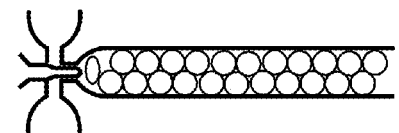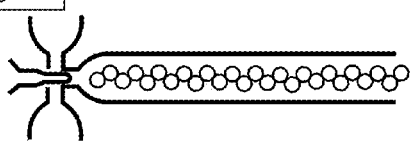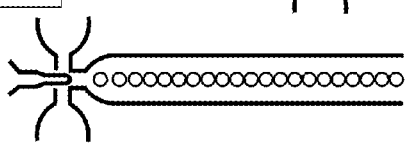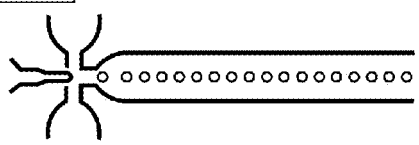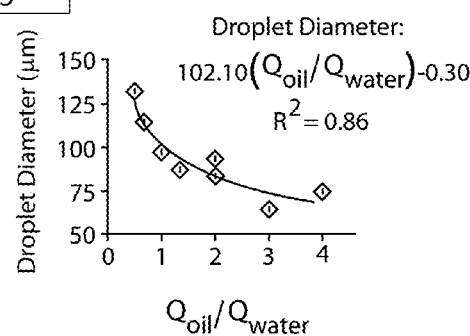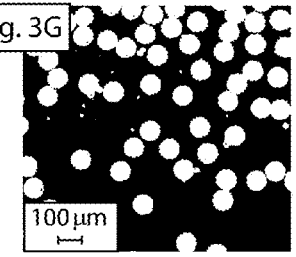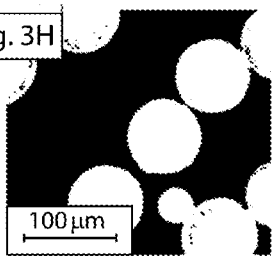

= MG-(VPGVG)$_{60}$(VPGAGVPGGG)$_{30}$HEDGHWDGSEHGY-G

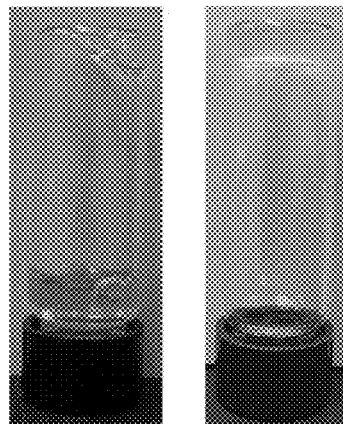
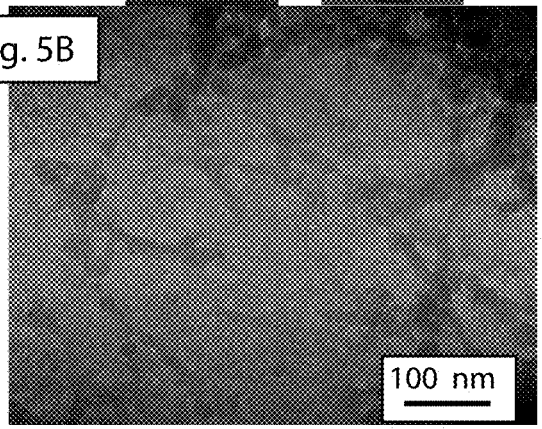
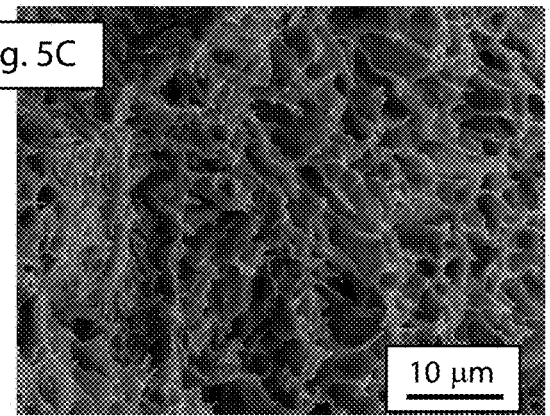

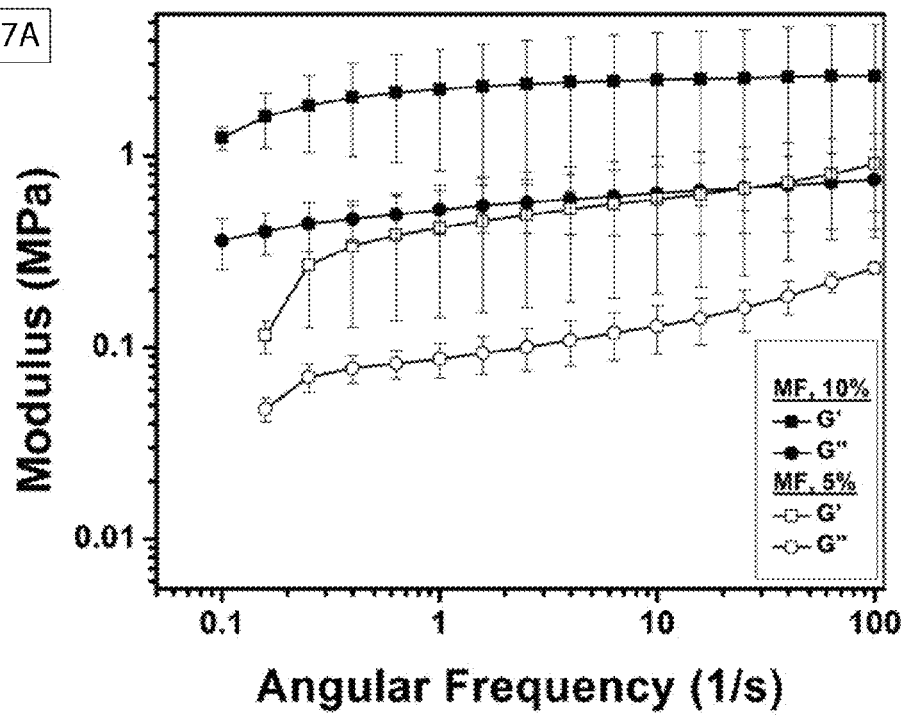
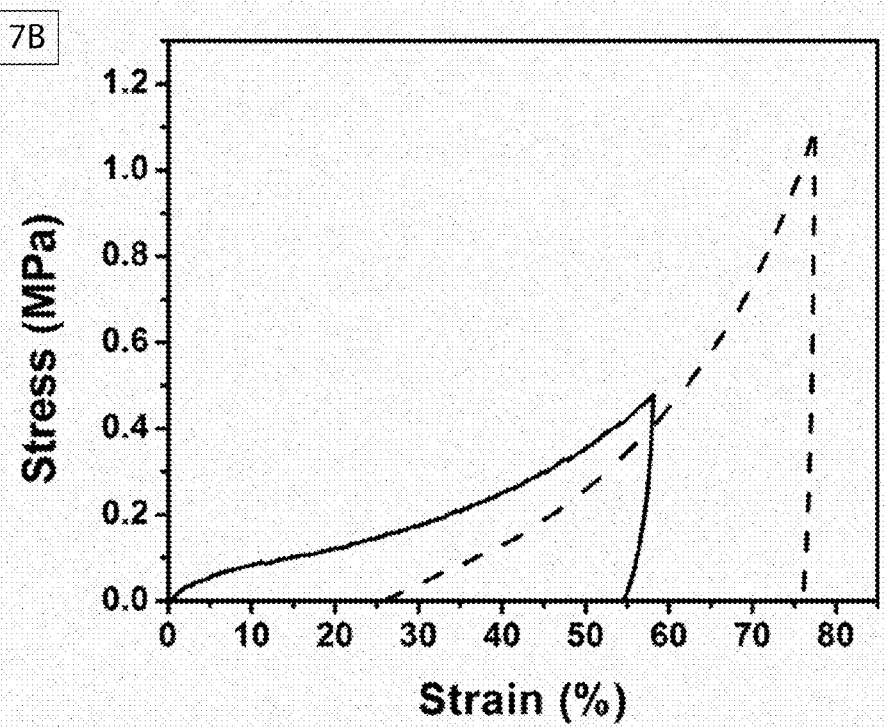

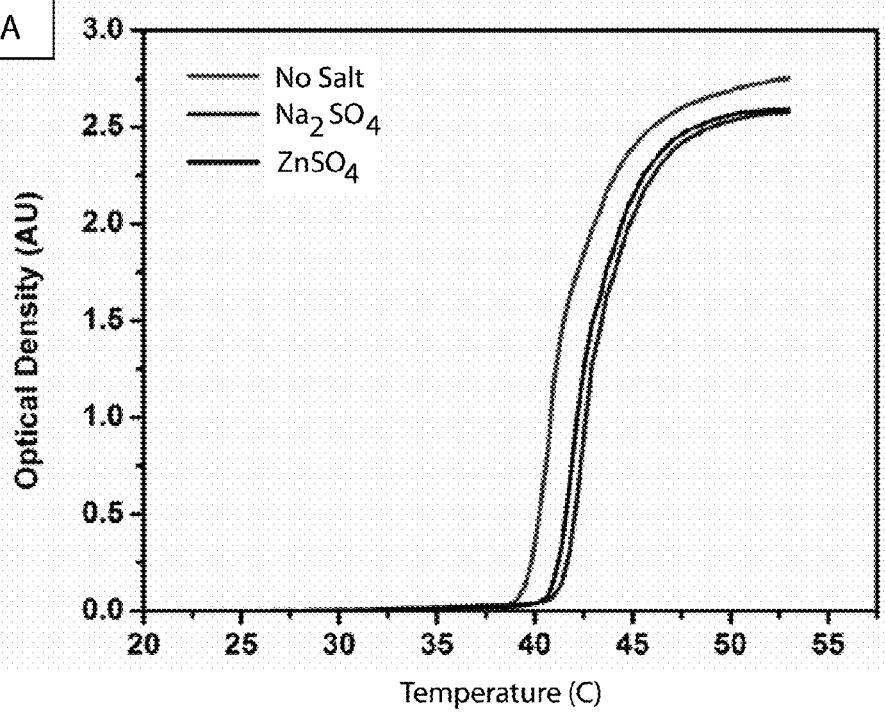
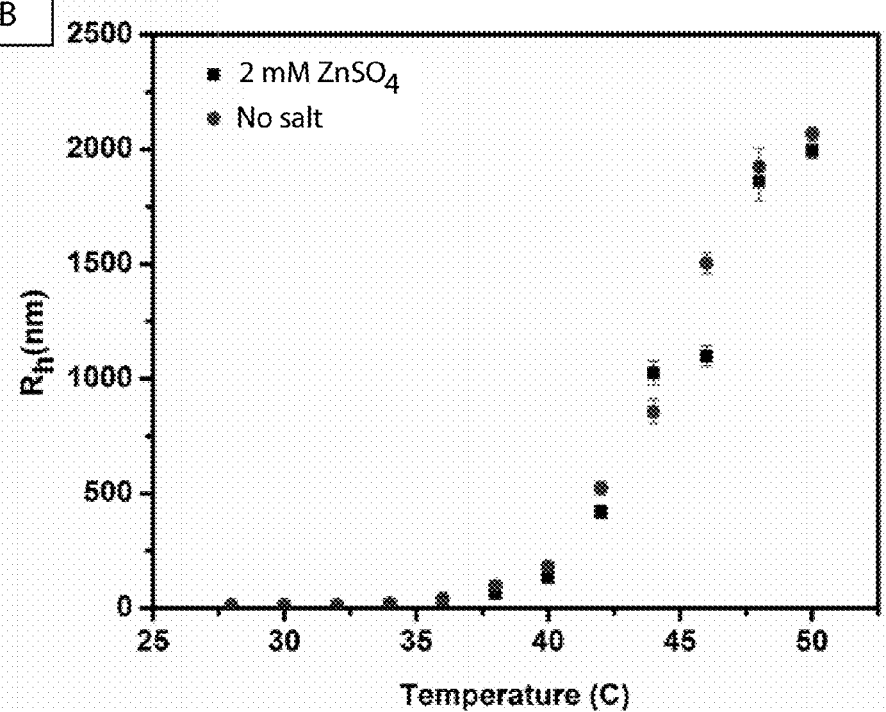

```
SEQUENCE LISTING

<160> NUMBER OF SEQ ID NOS: 6

<210> SEQ ID NO 1
<211> LENGTH: 5
<212> TYPE: PRT
<213> ORGANISM: Artificial
<220> FEATURE:
<223> OTHER INFORMATION: Synthetic sequence

<400> SEQUENCE: 1

Val Pro Gly Val Gly
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic sequence

<400> SEQUENCE: 2

Val Pro Gly Ala Gly Val Pro Gly Gly Gly
1               5                   10
```

```
<210> SEQ ID NO 3
<211> LENGTH: 13
<212> TYPE: PRT
<213> ORGANISM: Artificial Sequence
<220> FEATURE:
<223> OTHER INFORMATION: Synthetic sequence

<400> SEQUENCE: 3

His Glu Asp Gly His Trp Asp Gly Ser Glu His Gly Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic sequence

<400> SEQUENCE: 4

Val Pro Gly Ala Gly Val Pro Gly Val Gly
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic sequence

<400> SEQUENCE: 5

Val Pro Gly Val Gly Val Pro Gly Ala Gly
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic sequence

<400> SEQUENCE: 6

Val Pro Gly Ala Gly
1               5
```

HYDROGELS FORMED FROM POLYPEPTIDE MICELLES AND METHODS OF USE THEREOF

CROSS REFERENCE TO RELATED APPLICATIONS

The present application claims the benefit under 35 U.S.C. § 119(e) of U.S. Provisional Patent Application Ser. No. 62/134,672 filed on Mar. 18, 2015, the entire content of which is incorporated herein by reference.

FEDERAL FUNDING LEGEND

The presently disclosed subject matter was supported by Federal Grant Nos. DMR-1121107 and DGF1106401 awarded by the National Science Foundation. The U.S. Government has certain rights in the presently disclosed subject matter.

FIELD OF THE INVENTION

The presently disclosed subject matter generally relates hydrogels formed from polypeptide micelles, and methods of making and using the same.

BACKGROUND

Hydrogels are a common biomaterials platform employed for use as tissue substitutes, tissue scaffolds, and as drug delivery vehicles. Prior art application of hydrogels in these technologies has typically resulted in low efficacy due to poor material performance, such as weak mechanical properties and/or inefficient release. Thus, a need exists for hydrogels that exhibit enhanced mechanical properties and sustained release of micelles loaded with bioactive cargos.

SUMMARY

In some embodiments, the presently disclosed subject matter is directed to a hydrogel comprised of reversibly crosslinked micelles, the hydrogel comprising a plurality of a peptide polymer having a hydrophobic portion, a hydrophilic portion, and a peptide metal binding sequence near a terminus of the hydrophilic portion, wherein the peptide polymer is in the form of a plurality of micelles having the hydrophobic portion at a core of the micelles and the metal binding sequence at a surface of the micelles. The hydrogel further comprises a plurality of metal ions bound at the metal binding sequences, wherein the plurality of micelles are reversibly crosslinked through the bound metal ions.

In some embodiments, the presently disclosed subject matter is directed to a method of making a hydrogel comprised of reversibly crosslinked micelles, the method comprising heating a plurality of a peptide polymer having a hydrophobic portion, a hydrophilic portion, and a peptide metal binding sequence near a terminus of the hydrophilic portion, wherein the peptide polymer takes the form of a plurality of micelles having the hydrophobic portion at a core of the micelles and the metal binding sequences at a surface of the micelles. The method further comprises adding a plurality of metal ions to the micelles, wherein the plurality of micelles are reversibly crosslinked through the bound metal ions at the metal binding sequences.

In some embodiments, the presently disclosed subject matter is directed to a hydrogel loaded with a therapeutic molecule, the hydrogel comprising a plurality of a peptide polymer having a hydrophilic portion and a peptide metal binding sequence at a terminus of the hydrophilic portion; and a hydrophobic therapeutic agent attached near an opposing terminus of the hydrophilic portion, wherein the peptide polymer is in the form of a plurality of micelles having the hydrophobic therapeutic agent at a core of the micelles and the metal binding sequence at a surface of the micelles. The hydrogel further comprises a plurality of metal ions bound at the metal binding sequences, wherein the plurality of micelles are reversibly crosslinked through the bound metal ions.

In some embodiments, the presently disclosed subject matter is directed to a method of making a hydrogel loaded with a therapeutic agent, the method comprising attaching a hydrophobic therapeutic agent near a terminus of a hydrophilic portion of a plurality of a peptide polymer having a peptide metal binding sequence at an opposing terminus of the hydrophilic portion, wherein the peptide polymer takes the form of a plurality of micelles having the hydrophobic therapeutic agent at a core of the micelles and the metal binding sequences at a surface of the micelles. The method further comprises adding a plurality of metal ions to the micelles, wherein the plurality of micelles are reversibly crosslinked through the bound metal ions at the metal binding sequences.

In some embodiments, the presently disclosed subject matter is directed to a method for providing a therapeutic molecule to a subject, the method comprising administering a hydrogel to the subject. In some embodiments, the hydrogel comprises a plurality of a peptide polymer having a hydrophobic portion, a hydrophilic portion, a peptide metal binding sequence near a terminus of the hydrophilic portion, and a hydrophobic therapeutic agent attached to the hydrophobic portion, wherein the peptide polymer is in the form of a plurality of micelles having the hydrophobic portion and the hydrophobic therapeutic agent at a core of the micelles and the metal binding sequence at a surface of the micelles. The hydrogel further comprises a plurality of metal ions bound at the metal binding sequences, wherein the plurality of micelles are reversibly crosslinked through the bound metal ions.

In some embodiments, the presently disclosed subject matter is directed to a method for providing a therapeutic molecule to a subject, the method comprising administering a hydrogel to the subject. In some embodiments, the hydrogel comprises a plurality of a peptide polymer having a hydrophilic portion and a peptide metal binding sequence at a terminus of the hydrophilic portion, and a hydrophobic therapeutic agent attached near an opposing terminus of the hydrophilic portion, wherein the peptide polymer is in the form of a plurality of micelles having the hydrophobic therapeutic agent at a core of the micelles and the metal binding sequence at a surface of the micelles. The hydrogel further comprises a plurality of metal ions bound at the metal binding sequences, wherein the plurality of micelles are reversibly crosslinked through the bound metal ions.

BRIEF DESCRIPTION OF THE DRAWINGS

The previous summary and the following detailed description are to be read in view of the drawings, which illustrate particular exemplary embodiments and features as briefly described below. The summary and detailed descriptions, however, are not limited to only those embodiments and features explicitly illustrated.

FIGS. 3A-3E illustrate a droplet microfluidic device for generating monodisperse water droplets in accordance with some embodiments of the presently disclosed subject matter.

FIG. 3F is a graph of water droplet diameter as a function of $Q_{oil}/Q_{water}$ for water droplets produced using the device of FIGS. 3A-3E.

FIGS. 3G-3H are electron micrographs of monodisperse water droplets produced from the device illustrated in FIGS. 3A-3E.

FIG. 5A is an image of micelle-forming elastic-like polypeptide in micellar suspension before and after crosslinking.

FIG. 5B is a cryo-electron microscopy image of a hydrogel incipient network in accordance with some embodiments of the presently disclosed subject matter.

FIG. 5C is a scanning electron microscope image of a freeze-dried mature MiGel in accordance with some embodiments of the presently disclosed subject matter.

FIG. 7A is a graph of storage and loss modulus as a function of angular frequency for MiGels at two polymer concentrations.

FIG. 7B is a graph of cyclic compression and expansion of MiGels produced according to some embodiments of the presently disclosed subject matter.

FIG. 10A is a graph of the optical density as function of temperature of non-micelle forming elastin-like polypeptide in the absence and presence of salts.

FIG. 10B is a graph of the hydrodynamic radius as a function of temperature of non-micelle forming elastin-like polypeptide in the absence and presence of salt.

DETAILED DESCRIPTION

Figure 1A:
FIG. 1A is a representation of a peptide polymer that can be used in some embodiments of the presently disclosed subject matter.

The presently disclosed subject matter is directed to compositions, methods, and systems (e.g., platforms) comprising micro- and macro-hydrogels that are formed from polypeptide micelles. The disclosed systems exhibit enhanced mechanical properties that can be useful in a wide variety of applications. In addition, the disclosed systems can be used for controlled release of drug-loaded micelles and can be designed to reversibly assemble and disassemble on demand.

Unless otherwise defined, all technical terms used herein have the same meaning as commonly understood by one of ordinary skill in the art to which this disclosure belongs.

Following long-standing patent law convention, the terms "a," "an," and "the" refer to one or more when used in this application, including the claims. Thus, for example, reference to "a micelle" includes a plurality of micelles, unless the context clearly is to the contrary.

For the purposes of this specification and appended claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

The term "covalently crosslinked" as used herein refers to the formation of a covalent bond between reactive polymers that is stable in the presence of an ionic solution and/or is stable at high pH levels.

In the embodiment illustrated in FIG. 1, the terms "diblock polypeptide" and "peptide polymer" are used interchangeably for the purposes of the specification and claims.

The term "hydrogel" as used herein refers to a polymeric material that exhibits the ability to swell in water and retain a significant portion of water within its structure without dissolution.

The term "hydrophilic" as used herein refers to properties of a material that allow it to easily combine with a water molecule and/or allow it easily dissolve in water, and/or refers to polar properties of the material.

The term "hydrophobic" as used herein refers to properties of a material that do not allow it to easily combine with a water molecule and/or do not allow it easily dissolve in water, and/or refers to non-polar properties of the material.

As used herein, the term "linker" refers to an amino acid sequence that connects or links two peptide sequences.

As used herein, the term "micelle" refers to an aggregate of spherical molecules dispersed in a liquid wherein the aggregate comprises outward-facing hydrophilic head regions sequestering hydrophobic single tail regions in the micelle center.

The term "motif" as used herein refers to a set of amino acids conserved at specific positions along an aligned sequence of related proteins.

The term "polypeptide" or "peptide" or "protein" as used herein refers to a molecule composed of amino acid monomers linearly linked by amide bonds (peptide bonds). The terms "polypeptide", "protein" and "peptide" can be used interchangeably herein.

The descriptions herein are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

The systems described herein have potential applications that fill voids in current technologies. For example, the disclosed hydrogels can be used as stiff biomaterials capable of self-healing for use as tissue substitutes and tissue engineering scaffolds. Currently available hydrogel materials suffer from weak mechanical properties and/or the inability to self-heal upon damage, which can limit their use in high stress environments. The disclosed systems can also prove useful in nanomedicine, where treatments are generally in the form of systemic injections that often have low efficacy due to high clearance and poor targeting. In some embodiments, the presently disclosed subject matter includes a platform capable of slowly and controllably releasing nanoparticles loaded with drugs for sustained delivery and enhanced efficacy. The disclosed materials can be used to significantly enhance chemoembolization therapies as mechanically robust micro-gels with the ability to release nanoparticle loaded drugs. In each of these areas, the high performance mechanical properties and controlled release properties of the disclosed materials can be easily tailored by a number of synthetic variables, thereby enabling use in a variety of applications.

The present disclosure provides, in part, compositions, methods, and systems (e.g., platforms) comprising the same, the systems comprising, consisting of, or consisting essentially of micro- and macro-hydrogels that are formed from polypeptide micelles. These systems (1) have enhanced mechanical properties that may be useful in a wide variety of areas (such as, but not limited to, implant applications), (2) can be used for controlled release of drug-loaded micelles, and (3) can be designed to reversibly assemble and disassemble on demand.

The presently disclosed subject matter can be distinguished in several ways from prior art gel-based platforms for drug delivery applications. For example, prior systems for drug therapy in the realm of nanomedicine rely on the use of bolus, systemic single injections for treatment. The majority of these nanoparticle systems suffer from low efficacy due to high clearance rates and low accumulation levels at the site of interest. The disclosed system, in comparison, provides sustained release of nanoparticles thereby enabling higher long-term accumulation at the site of interest.

The disclosed method utilizes a biologically inspired approach that enables the constituent proteins to be genetically encoded (e.g., micelle size, micelle core properties, micelle surface, crosslinking density, micelle cargo). Various external variables (e.g., crosslinking metals, polypeptide concentration) can be controlled that (in conjunction with controlling micelle characteristics) enable precise control of the mechanical properties of the resultant gels. The disclosed methods are useful for creating mechanically tunable gels that are robust enough to withstand harsh in vivo environments. Furthermore, the noncovalent interactions between micelles enables reversible network formation on-demand.

The disclosed gel networks can be extended to include interpenetrated proteins that are covalently crosslinked. Such a hybrid homopolymer-micelle gel is believed to be novel in the protein-based hydrogel community. The dual network platform enables passive control of the release of micelles with simple changes in the processing variables (e.g., covalently crosslinkable polymer size, covalent crosslinking molecules, covalent crosslink density), which is a powerful technique for sustaining micelle release.

The creation of microgel geometries comprised of the disclosed hybrid network platforms is the first demonstration of such robust micro-gels for sustained delivery of micelles. The particles, which exhibit robust mechanical properties and tailorable micelle release, are excellent vehicles for chemoembolization therapies[1-3]. Traditional chemoembolization particles are ineffective due to weak mechanical properties and uncontrollable release of small molecule drugs that are rapidly cleared due to their insolubility[1,4-6].

Figure 1B:
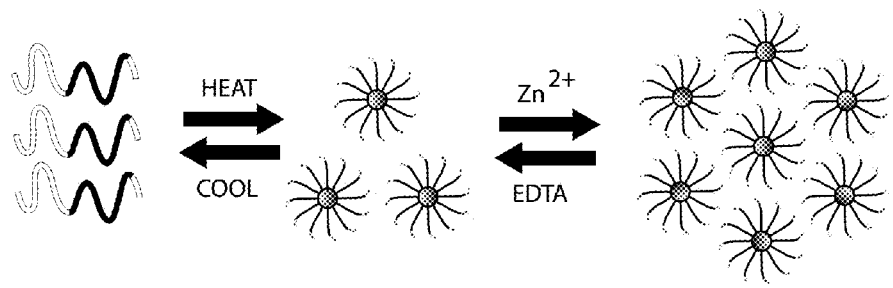
FIG. 1B is a schematic of stimulus-triggered assembly of peptide polymers into micelles in accordance with some embodiments of the presently disclosed subject matter.

Hydrogels produced from micelles can be formed by crosslinking the surface of the micelles. The constituent micelles contain a metal-binding peptide displayed on their surface. The disclosed peptide polymer can be designed to include a hydrophobic portion (such as repeats of VPGVG (SEQ ID NO: 1)), a hydrophilic portion (such as repeats of VPGAGVPGGG (SEQ ID NO: 2)), and a peptide metal binding sequence presented at the hydrophilic terminus (such as HEDGHWDGSEHGY (SEQ ID NO: 3) taken from the consensus zinc-binding sequence found in the active sites of matrix metalloproteinases). The peptide metal binding sequence functions to bind metal ions, wherein the addition of divalent ions results in the formation of coordination bonds between micelles, which in turns forms a gel. FIG. 1 contains a schematic description of this strategy and the details of this method are described in detail below. Particularly, the genetic encoding of various amino acids (FIG. 1A) enables stimulus-triggered (heat, for example) assembly of polypeptides into micelles (FIG. 1B). The micelles display metal-binding peptides at their surface, which enables their formation into gels with the addition of zinc or other metal ions.

Thus, as illustrated in FIGS. 1A and 1B, the presently disclosed subject matter comprises a hydrogel comprised of reversibly crosslinked micelles. Particularly, in some embodiments, the hydrogel comprises a plurality of a peptide polymer having a hydrophobic portion, a hydrophilic portion, and a peptide metal binding sequence near a terminus of the hydrophilic portion, wherein the peptide polymer is in the form of a plurality of micelles having the hydrophobic portion at a core of the micelles and the metal binding sequence at a surface of the micelles. In some embodiments, the hydrogel further comprises a plurality of metal ions bound at the metal binding sequences, wherein the plurality of micelles are reversibly crosslinked through the bound metal ions.

In some embodiments, the disclosed hydrogel can be constructed by heating a plurality of a peptide polymer having a hydrophobic portion, a hydrophilic portion, and a peptide metal binding sequence near a terminus of the hydrophilic portion, wherein the peptide polymer takes the form of a plurality of micelles having the hydrophobic portion at a core of the micelles and the metal binding sequences at a surface of the micelles. The method further comprises adding a plurality of metal ions to the micelles, wherein the plurality of micelles are reversibly crosslinked through the bound metal ions at the metal binding sequences. In some embodiments, the peptide polymer further comprises a hydrophobic therapeutic agent attached to the hydrophobic portion, wherein the hydrophobic therapeutic agent is at the core of the micelles along with the hydrophobic portion. In some embodiments, the method further comprises adding a plurality of a polymer and a crosslinking agent, wherein the plurality of polymers are covalently crosslinked to each other to form an interpenetrating mesh consisting essentially of the covalently crosslinked polymers, wherein the interpenetrating mesh surrounds the reversibly crosslinked micelles without being covalently attached to the micelles.

In some embodiments, the disclosed peptide polymer comprises a synthetic peptide, a naturally derived peptide, and/or a hybrid synthetic-naturally derived peptide. In some embodiments, the peptide polymer comprises an elastin-like polypeptide (ELP). In some embodiments, the hydrophobic portion of the peptide polymer comprises 40 to 80 repeats of a VPGVG (SEQ ID NO: 1) peptide motif, such as (VPGVG; (SEQ ID NO: 1))$_{60}$. In some embodiments, the hydrophilic portion of the peptide polymer comprises 10 to 50 repeats of a VPGAGVPGGG (SEQ ID NO: 2) peptide motif, such as (VPGAGVPGGG; (SEQ ID NO: 2))$_{30}$. In some embodiments, the peptide metal binding sequence comprises a motif HEDGHWDGSEHGY (SEQ ID NO: 3) and the metal comprises one or more of transition metals $Zn^{2+}$, $Ni^{2+}$, or $Cu^{2+}$.

In some embodiments, the peptide polymer further comprises a hydrophobic therapeutic agent attached to the hydrophobic portion at the core of the micelles. The hydrophobic agent can be attached to the hydrophobic portion through a linker, wherein the linker includes an enzymatic cleavage site and/or a pH sensitive cleavage site to allow for release of the hydrophobic therapeutic agent from the micelle.

In some embodiments, the disclosed hydrogel comprises an interpenetrating mesh consisting essentially of covalently crosslinked polymers, wherein the mesh surrounds the reversibly crosslinked micelles without being covalently attached to the micelles. The covalently crosslinked polymers can comprise polypeptides, elastin-like polypeptides (ELP), biopolymers, synthetic polymers, branched polymers, and combinations thereof. In some embodiments, the covalently crosslinked polymers comprise the repeating peptide motif ((VPGAGVPGVG; (SEQ ID NO: 4))$_5$GKG)$_8$.

In some embodiments, the presently disclosed subject matter is directed to a method for providing a therapeutic molecule to a subject. Particularly, the method comprises administering a hydrogel to a subject, wherein the hydrogel comprises a plurality of a peptide polymer having a hydrophobic portion, a hydrophilic portion, a peptide metal binding sequence near a terminus of the hydrophilic portion, and a hydrophobic therapeutic agent attached to the hydrophobic portion. The peptide polymer can be in the form of a plurality of micelles having the hydrophobic portion and the hydrophobic therapeutic agent at a core of the micelles and the metal binding sequence at a surface of the micelles. The hydrogel further comprises a plurality of metal ions bound at the metal binding sequences, wherein the plurality of micelles are reversibly crosslinked through the bound metal ions. In some embodiments, the hydrogel further comprises an interpenetrating mesh consisting essentially of covalently crosslinked polymers, and the mesh surrounds the reversibly crosslinked micelles without being covalently attached to the micelles. In some embodiments, the hydrophobic therapeutic agent can be attached to the hydrophobic portion through a linker that includes an enzymatic cleavage site and/or a pH sensitive cleavage site to allow for release of the hydrophobic therapeutic agent from the micelle In some embodiments, the disclosed hydrophobic therapeutic agent comprises one or more of a small molecule, drug, or a peptide. In some embodiments, the hydrogel can be in the form of a microsphere and the administering can be through intravenous injection, such as through injection into a tissue, an organ, a vein, and/or an artery for localized delivery of the therapeutic agent. In some embodiments, the therapeutic agent can be provided to the subject over a sustained period of time of about 1 day to about 30 days, about 1 day to about 20 days, about 1 day to about 10 days, or about 1 day to about 4 days.

The disclosed hydrogels exhibit enhanced mechanical properties as compared to existing bio-based hydrogels formed via non-covalent interactions. The high stiffness of the gels can be tuned by varying input parameters, such as protein and crosslinker concentration, which are important for in vivo efficacy. Further, the structure of the disclosed hydrogels has been characterized to verify the existence of micelles within crosslinked gels, thereby enabling the disclosed platform to be used for releasing micelles loaded with drugs, which has been previously shown[7].

Mechanically robust hydrogels have been constructed herein to enable controlled and sustained release of micelles from a gel network (FIG. 2). In the disclosed system, proteins capable of sequestering hydrophobic small molecules (such as chemotherapeutic drugs) within micelles have been engineered. The micelles display metal-binding motifs on their surface, thus allowing their formation into mechanically robust hydrogels upon coordination of metal ions. In some embodiments, the micellar network can be interpenetrated with a covalently crosslinkable homopolymer protein to create a mesh around the crosslinked micelles without being covalently attached to the micelles. By doing so and applying a chemical potential with respect to metal concentration between the gel and the surrounding, the release of micelles can be sustained for several days. Simple changes in the gel variables (e.g., micelle concentration, homopolymer protein concentration, metal ion type and concentration, covalent crosslinker concentration, chemical potential) enable the release rate for a particular application to be tuned. In some embodiments, the covalently crosslinkable homopolymer protein comprises elastin-like polypeptides (ELP), biopolymers, synthetic polymers, branched polymers, and combinations thereof.

Figure 2A:
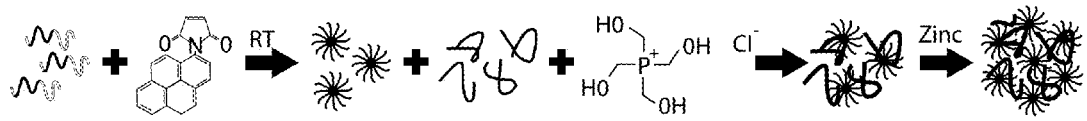
FIG. 2A is a schematic illustrating the formation of gels comprised of metal crosslinked micelles loaded with small molecules interpenetrated with covalently-crosslinked homopolymer proteins in accordance with some embodiments of the presently disclosed subject matter.

FIG. 2A is a schematic illustrating the formation of gels comprised of metal-crosslinked micelles loaded with small molecules that are interpenetrated with covalently-crosslinked homopolymer proteins. For example, in some embodiments, a polypeptide containing periodic lysine residues (such as (VPGAGVPGVG; (SEQ ID NO: 4))$_5$GKG)$_8$) can be used for covalent crosslinking of an interpenetrating network (ELF-Lys).

Figure 2B:
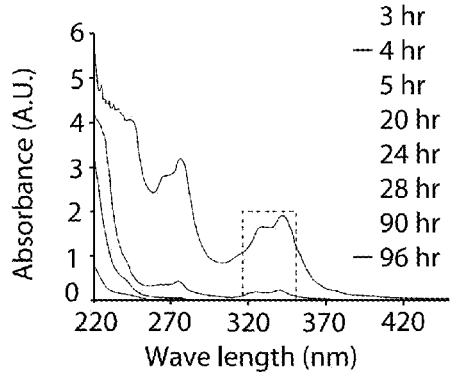
FIG. 2B is a graph of UV-Visible spectrophotometry curves of supernatant solutions containing dual crosslinked micelle homopolymer hydrogels at various timepoints.
Figure 2D:
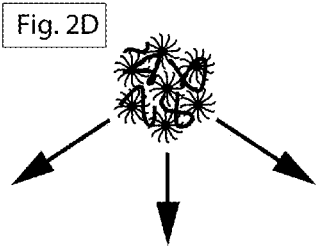
FIGS. 2D-2F is a schematic illustrating dual crosslinked gels that release micelles at different rates based on the chemical potential between the gel and the surrounding environment.
Figure 2E:
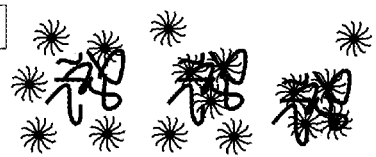
Figure 2F:
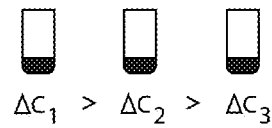
Figure 2C:
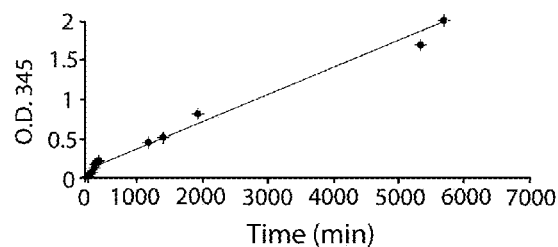
FIG. 2C is a graph of the optical density measurements of supernatant solutions containing dual crosslinked micelle homopolymer hydrogels.

FIG. 2B illustrates UV-Visible spectrophotometry curves of supernatant solutions containing dual-crosslinked micelle-homopolymer hydrogels at various time points. A chemical potential between the hydrogel and the supernatant drives the sustained release of micelles, which exhibit a peak in the dashed region. Optical density measurements at 345 nm indicate a linear release of micelles up to 4 days, as shown in FIG. 2C. FIG. 2D is a schematic illustrating dual-crosslinked gels that release micelles at different rates (FIG. 2E) based on the chemical potential between the gel and the surrounding environment (FIG. 2F). The larger the concentration difference between the gel and the surrounding, the faster the release of micelles.

Thus, in some embodiments, the presently disclosed subject matter is directed to a hydrogel loaded with a therapeutic molecule, wherein the hydrogel comprises a plurality of a peptide polymer having a hydrophilic portion and a peptide metal binding sequence at a terminus of the hydrophilic portion. The peptide polymer further comprises a hydrophobic therapeutic agent attached near an opposing terminus of the hydrophilic portion. The peptide polymer is in the form of a plurality of micelles having the hydrophobic therapeutic agent at a core of the micelles and the metal binding sequences at a surface of the micelles. The hydrogel further comprises a plurality of metal ions bound at the metal binding sequences, wherein the plurality of micelles are reversibly crosslinked through the bound metal ions.

In some embodiments, the disclosed hydrogel further comprises an interpenetrating mesh consisting essentially of covalently crosslinked polymers, wherein the mesh surrounds the reversibly crosslinked micelles without being covalently attached to the micelles. The covalently crosslinked polymers can comprise polypeptides, elastin-like polypeptides (ELP), biopolymers, synthetic polymers, or branched polymers, and combinations thereof. In some embodiments, the covalently crosslinked polymers can comprise the repeating peptide motif ((VPGAGVPGVG; (SEQ ID NO: 4))$_5$GKG)$_8$.

In some embodiments, the peptide polymer comprises a synthetic peptide, a naturally derived peptide, and/or a hybrid synthetic-naturally derived peptide. In some embodiments, the peptide polymer comprises an elastin-like polypeptide (ELP). The hydrophilic portion of the peptide polymer can comprise about 60 to 100 repeats of a VPGAG (SEQ ID NO: 6) peptide motif, such as (VPGAG; (SEQ ID NO: 6))$_{80}$. In some embodiments, the peptide metal binding site comprises a motif HEDGHWDGSEHGY (SEQ ID NO: 3) and the metal comprises one or more of transition metals $Zn^{2+}$, $Ni^{2+}$, or $Cu^{2+}$.

In some embodiments, the hydrophobic therapeutic agent can comprise one or more of a small molecule, a drug, or a peptide. In some embodiments, the hydrophobic therapeutic agent can be attached to the hydrophilic portion through a linker, wherein the linker includes an enzymatic cleavage site and/or a pH sensitive cleavage site to allow for release of the therapeutic agent from the micelle.

In some embodiments, the presently disclosed subject matter is directed to a method of making a hydrogel loaded with a therapeutic agent, wherein the method comprises attaching a hydrophobic therapeutic agent near a terminus of a hydrophilic portion of a plurality of a peptide polymer having a peptide metal binding sequence at an opposing terminus of the hydrophilic portion. The peptide polymer can take the form of a plurality of micelles having the hydrophobic therapeutic agent at a core of the micelles and the metal binding sequences at a surface of the micelles. The method further comprises adding a plurality of metal ions to the micelles, wherein the plurality of micelles are reversibly crosslinked through the bound metal ions at the metal binding sequences. In some embodiments, the method further comprises adding a plurality of a polymer and a crosslinking agent, wherein the plurality of polymers are covalently crosslinked to each other to form an interpenetrating mesh consisting essentially of the covalently crosslinked polymers, wherein the interpenetrating mesh surrounds the reversibly crosslinked micelles without being covalently attached to the micelles.

In some embodiments, the presently disclosed subject matter is directed to a method for providing a therapeutic molecule to a subject, the method comprising administering a hydrogel to the subject, wherein the hydrogel comprises a plurality of a peptide polymer having a hydrophilic portion and a peptide metal binding sequence at a terminus of the hydrophilic portion, and a hydrophobic therapeutic agent attached near an opposing terminus of the hydrophilic portion, wherein the peptide polymer is in the form of a plurality of micelles having the hydrophobic therapeutic agent at a core of the micelles and the metal binding sequences at a surface of the micelles. The hydrogel further comprises a plurality of metal ions bound at the metal binding sequences, wherein the plurality of micelles are reversibly crosslinked through the bound metal ions. In some embodiments, the hydrogel further comprises an interpenetrating mesh consisting essentially of covalently crosslinked polymers, wherein the mesh surrounds the reversibly crosslinked micelles without being covalently attached to the micelles. The hydrophobic therapeutic agent can be attached to the hydrophilic portion through a linker, wherein the linker includes an enzymatic cleavage site and/or a pH sensitive cleavage site to allow for release of the hydrophobic therapeutic agent from the micelle.

In some embodiments, the hydrophobic therapeutic agent comprises one or more of a small molecule, a drug, or a peptide. In some embodiments, the hydrogel can be in the form of a microsphere and the administering can be through intravenous injection into a tissue, an organ, a vein, and/or an artery for localized delivery of the therapeutic agent. The therapeutic agent can be provided to the subject over a sustained period of about 1-30 days, 1-20 days, 1-10 days, or 1-4 days.

To form hydrogels, droplet based microfluidic devices can be used to template microscale spherical gels. FIGS. 3A-3F illustrate a suitable droplet microfluidic device for generating monodisperse water droplets. The droplets serve as templates for forming crosslinked protein microgels, as shown in FIGS. 3G-3H. Mechanically robust polypeptide microgels are excellent candidates for use in chemoembolization treatments where the primary objective is vasculature occlusion[8]. Robust microgels capable of releasing micelles have the potential to (1) occlude vasculature and cut-off blood supply to tumors and (2) sustain release of highly toxic drugs (e.g., doxorubicin) that synergistically act to combat tumors in various types of cancer (e.g., liver). The production of robust protein microgels is amenable to scale-up with the use of membrane emulsifiers[9], thus making the disclosed technology realizable on an industrial scale.

The scope of the presently disclosed subject matter is not limited to the above disclosures and can be easily modified in a variety of ways. For example, micelles made from materials other than genetically engineered proteins, including naturally derived biopolymers and hybrid synthetic-natural polymers, can be created. In addition, a variety of metal-ligand complexes with varying binding affinities can be used. Other covalently crosslinkable polymers and biopolymers (e.g., branched polymers) to create the interpenetrating mesh around the crosslinked micelles can also be employed. Various covalent crosslinkers (e.g., photocrosslinkers) can be used to finely tune the mesh size of the interpenetrating network. The cargo used within the core of the micelles can be changed to include various small molecules, drugs and peptides. Stimulus-responsive materials (e.g., pH responsive, light responsive, magnetic responsive) can be used to control the release of micelles on-demand and/or to disassemble the micelles on-demand to deliver cargo. Enzymatically degradable sites can be incorporated within the gel to further tune micelle release kinetics. Gels made of synthetic polymers and hybrid synthetic-natural polymeric gels can be created. Other environmentally responsive biopolymers with LOST or UCST phase behaviors to tune micelle formation and release can be created. Various crosslinking chemistries (e.g., mechanoresponsive crosslinkers) can be used to create shear-thinning gels that can be injected into a site of interest for injectable depots. Environmentally responsive assemblies (e.g., pH responsive moieties) can be used to create injectable materials that undergo a sol-gel transition.

The simplicity with which the disclosed hydrogels can be formed and tuned is advantageous over existing gel platforms for drug delivery applications. Particularly, the disclosed hydrogels can be produced in large quantities, making them amenable for scale-up to industrial level manufacturing. Furthermore, the gels have long shelf lives under ambient conditions. Taken together, these attributes increase profit margins for manufactures and enable wide deployment of the disclosed technology.

The disclosed hydrogels can find utility in a wide variety of areas. For example, they can be used as implantable and injectable depots for the controlled, sustained release of micelles as drug delivery vehicles. Sustaining micelle release holds promise for enhanced efficacy of nanomedicine therapies. The gels can also be used as mechanically robust scaffolds for engineered tissue replacements and tissue engineering scaffolds. The high stiffness of these hydrogels, combined with their dynamic interactions, make them suitable for tissue rehabilitation applications where high loads are needed. Engineered protein microgels can be used for chemoembolization materials. Mechanically robust microgels are excellent embolization materials. This, combined with sustained release of micelles, holds promise for effective chemoembolization therapies for treatment of a variety of solid tumors.

Continuing, the disclosed compositions and methods can be used as self-healing materials with rapid healing response times for high load bearing applications (e.g., within joint replacements). The disclosed compositions can further be used as reversible tissue scaffolds with dynamic re-configurability and can be used as hierarchically structured platforms for building tissue replacements with organization on multiple length scales. Injectable or implantable hydrogels can be used for regeneration of bone, spinal cord, cartilage and other tissues. Gels containing micelles loaded with various cargos can be used for synergistic therapeutics. Cell responsive scaffolds can be used wherein different micelles respond to various cell signals (e.g., secretion of proteases) in the form of a feedback system. Stiff hydrogels containing various binding moieties can be used for controlled cellular adhesion. The disclosed materials can be used as sealants for promoting wound healing. Hydrogel beads containing various chemicals (e.g., nutrients, antibiotics) with sustained release can be used in agricultural processes, including stimulus-responsive beads for environmentally responsive release of the above-mentioned chemicals. The disclosed materials can further be used in drug delivery applications.

EXAMPLES

The following Examples provide illustrative embodiments. In light of the present disclosure and the general level of skill in the art, those of ordinary skill in the art will appreciate that the following Examples are intended to be exemplary only and that numerous changes, modifications, and alterations can be employed without departing from the scope of the presently disclosed subject matter.

Advances in molecular biology and synthetic chemistry have enabled the development of engineered proteins and polymers that are finding their way into a variety of applications in medicine and biotechnology, from pharmaceuticals and regenerative medicine[12] to separations[13] and biosensing.[14] Hydrogels based on engineered peptides and proteins have been studied extensively because of their biocompatibility and the ease with which biofunctionality (typically incorporated as one or more copies of a fused bioactive protein or peptide) can be encoded into the systems at the genetic level.[10a, 15] The majority of efforts to engineer bio-hydrogels have focused on creating covalently crosslinked networks because of their mechanical stability.[16] However, covalently crosslinked bio-hydrogels are not always ideal because of (i) their often complex synthesis, which in some cases results in the formation of toxic by-products from the crosslinking reaction, and (ii) their inherently static and non-reversible crosslinks.[17] The irreversibility can impede the remodeling of the hydrogels in a biological environment, and in vivo can potentially lead to cell death, induction of inflammatory responses, and ultimately failure of implanted devices.[16,18]

As an alternative, efforts have focused on the synthesis of bio-hydrogels based on non-covalent (electrostatic, hydrophobic, ionic, coordination or hydrogen-bonded) crosslinking.[16] These intermolecular interactions are generally reversible, are not typically associated with toxic by-products, and can result in easy hydrogel formation, good biocompatibility, and the potential for dynamic remodeling.[19] However, most of the non-covalently cross-linked bio-hydrogels reported to date are mechanically weak,[16,20] unstable, and can be permanently damaged even when they are subjected to relatively low forces, attributes which limit their use in many in vivo applications. Such limitations have been circumvented to a certain extent in non-peptide based hydrogels by the design of double network hydrogels,[21] hydrogels made of polymers mixed with inorganic nanoparticles,[22] and the use of self-assembling hierarchical structures, including micelles[23],[24][25].

During the past decade, several groups have studied the use of polymeric micelles to introduce order and functionality into hydrogels using a variety of materials and crosslinking techniques.[22-24,26] In early work, polymeric micelles formed from synthetic peptide polymers were immobilized on surfaces to induce anti-fouling functionality to the surface. Later, micellar particles were used as an additive to a polymeric hydrogel without affecting the crosslinking mechanism, with the aim of introducing drug loading capability to the gels[27]. Micellar hydrogels[27b,28] are a class of reversibly crosslinked materials that exhibit interesting rheological behavior in which control over their viscoelastic response can be useful in rheological modification for coating applications.[24] Almost all of the prior studies have used self-assembling synthetic polymers as the building blocks of micellar gels and the mechanical characteristics of these gels have thus far not been on par with the mechanical properties of naturally derived hierarchically structured gel-like materials[24][29]. Hartgerink et al. used engineered polypeptides instead of synthetic polymers to make cylindrical micelles that were then covalently crosslinked into a biohydrogel scaffold to promote hydroxyapatite growth, but did not show enhanced mechanical properties prior to mineralization.[30] Wright et al. studied morphological characteristics of hydrogels made from hydrophobic interactions between genetically engineered amphiphilic elastin-like polypeptides and revealed the filamentous microstructure of such gels but did not investigate their mechanical properties.[31]

Described herein is a bio-inspired, engineered peptide polymer that can be reversibly crosslinked into a micellar hydrogel (a MiGel) with enhanced mechanical properties. The disclosed peptide polymer is inspired by the following design elements found in biological materials: (1) macromolecular subunits that (2) self-organize at the nanoscale[32] (3) into a hierarchical organization that yields a reversible network structure that gives rise to enhanced mechanical properties.[32-33] Examples of such materials include collagen,[34] actin microfilaments[35] and microtubules.[36] At the lowest dimensional scale, the building block of the MiGel is an environmentally responsive, peptide polymer that can be thermally triggered to self-assemble into spherical micelles. The peptide polymer can be designed with a transition metal binding peptide at the hydrophilic terminus of the polypeptide, such that a high density of metal coordination sites is presented on the surface of the micelles. For example, as illustrated in FIG. 1a, in some embodiments, the peptide polymer can comprise the sequence (VPGVG; (SEQ ID NO: 1))$_{60}$(VPGAGVPGGG; (SEQ ID NO: 2))$_{30}$HEDGHWDGSEHGY(SEQ ID NO:3), where VPGVG (SEQ ID NO: 1) represents the hydrophobic portion of the peptide polymer, VPGAGVPGGG (SEQ ID NO: 2) represents the hydrophilic portion of the peptide polymer, and HEDGHWDGSEHGY (SEQ ID NO:3) represents the peptide metal binding sequence.

At the second level of hierarchical structure, the micelles are reversibly crosslinked through metal coordination bonds into a higher order structure—a macroscopic hydrogel. Metal coordination was selected herein for reversible crosslinking, as it is exploited by nature for non-covalent, reversible organization of biological structures such as crosslinked byssal threads (strong, stiff structural fibers used by mussels to attach to rocks and other substrata).[38]

To create the hierarchical materials, a stimulus (such as heat) can be used to trigger the self-assembly of recombinant polypeptides into monodisperse micelles that display transition metal coordination motifs on their surfaces. For example, a MiGel can be rapidly formed by the addition of $Zn^{2+}$ to a colloidal suspension of the micelles. The hydrogel is stabilized by van der Waals and hydrophobic interactions in the core of the micelles, and by reversible metal coordination between micelles. In comparison to previously reported non-covalently crosslinked hydrogels, such MiGels exhibit very high moduli and can be reversibly disassembled to their micellar components through the addition of a strong metal ion chelator (such as EDTA). Further, MiGels can rapidly self-heal and their stiffness can be tuned by changing the polypeptide concentration. The disclosed bio-inspired method for creating robust, hierarchically ordered biomaterials can be used to generate new platforms for a variety of biomedical applications, such as tissue engineering, drug delivery, wound dressings and biosensing.

EXPERIMENTAL

Materials

The pET24+ expression vector was purchased from Novagen (Madison, Wis.). Restriction enzymes, ligation and dephosphorylation enzymes and were purchased from New England Biolabs (Ipswich, Mass.). BL21 *E. coli* cells were purchased from Bioline (Taunton, Mass.). All salts were purchased from Alfa Aesar (Ward Hill, Mass.). *E. coli* cell cultures were grown in TB media purchased from MO BIO laboratories Inc. (Carlsbad, Calif.). DNA extraction kits, DNA gel purification kits were purchased from Qiagen Inc. (Germantown, Md.). N-(1-Pyrenyl)maleimide and Tetrakis (hydroxymethyl) phosphonium chloride (THPC) were purchased from Sigma Aldrich.

ELP Gene Synthesis. Elastin-like polypeptide (ELP) genes were constructed using the recursive directional ligation by plasmid reconstruction method (PRe-RDL). The gene for (VPGAG; (SEQ ID NO: 6))$_{80}$ was modified by appending an N-terminal leader that encodes for the $Zn^{2+}$-binding peptide (as described herein) and a C-terminal trailer that encodes for eight repeats of a (GGC) peptide sequence. In some embodiments, the peptide polymer comprises from 60-100 repeats of a VPGAG peptide motif. A modified pET24+ expression vector was singly digested with a BseRI restriction enzyme. An annealed oligonucleotide encoding for the (1) metal-binding domain and (2) GGC repeat motif were separately ligated. The plasmid was digested with BseRI and BglII restriction enzymes to produce a trailer "A or B cut". The plasmid containing the (VPGAG)$_{80}$ gene was digested with AcuI and BglII restriction enzymes. The leader and trailer sequences were ligated to the digested (VPGAG; (SEQ ID NO: 6))$_{80}$ sequence to produce the "His-ELP-cys" sequence. The final sequence of the polypeptide as confirmed by gene sequencing was: HEDGHWDGSEHGY(SEQ ID NO:3)-(VPGAG; (SEQ ID NO: 6))$_{80}$-(GGC)$_8$. Additionally, using the same molecular biology techniques, a polypeptide containing periodic lysine residues was constructed to be used for covalent crosslinking of an interpenetrating network (ELP-Lys). The sequence of the ELP-Lys polypeptide was: ((VPGAGVPGVG; (SEQ ID NO: 4))$_5$GKG)$_8$.

Gene Expression and ELP Purification.

The ELP genes were transformed into chemically competent E. coli BL21 cells and incubated overnight. A single E. coli colony was used to inoculate a starter culture of sterilized TB media, supplemented with kanamycin. The culture was incubated overnight at 37° C. and 220 to 250 rpm. The starter culture was used to inoculate sterilized TB media in 4 L flasks, each containing 1 L of media supplemented with 45 µg/ml of kanamycin. The media was incubated at 37° C. and 220 rpm for 6 to 8 hours before inducing with 0.1 mM IPTG. The cultures were then shaken overnight at 37° C. before harvesting and centrifuging at 4° C. and 4000 rpm for 20 minutes. The ELPs were purified from the harvested cells by first lysing the cells via sonication for 3 minutes at pulses of 10 seconds on and 30 seconds off to prevent the solution from overheating. The ELPs were purified from the soluble fraction of the cell lysate by inverse transition cycling (ITC)[64], a process of centrifugation at high and low temperature to remove any cellular debris and other impurities from the ELP of interest.

ELP Characterization.

The purity and molecular weight of the purified proteins were characterized by 10-20% gradient Tris-Glycerol SDS-PAGE (Thermo Scientific, CA). The concentration of the ELP solution was determined by weighing the ELP after it had been lyophilized and resuspending in a known volume of 1× phophase buffered saline (PBS). The release kinetics of the small molecule loaded nanoparticles from the gel matrices were studied using UV-vis spectroscopy (Cary 300, Agilent Technology).

Hydrogel Formation.

For each hydrogel batch 6 identical gels (1 cm×1 cm×0.3 cm) were cast in a non-porous, non-adhesive Teflon mold in several sequential steps. First, N-(1-Pyrenyl)maleimide (a model hydrophobic small molecule drug) was conjugated to the C the C-terminal cysteines on the "His-ELP-cys" to create an asymmetric amphiphile that self-assembled into micelles, with the small molecule comprising the core and the ELP and $Zn^{2+}$-binding domain comprising the surface. The micelles (variable concentration from 2-5 wt %) were mixed with the ELP-lys polypeptides to enable the formation of an interpenetrating network. Next, 15 wt % ELP-lys polypeptides were covalently crosslinked to form a hydrogel scaffold through the addition of THPC (1:1 molar ratio of THPC arms to lysine residues), a small molecule that spontaneously forms stable covalent bonds with lysine residues[65]. The reaction was allowed to proceed to completion for 2 hours at room temperature. The hydrogels were then cut out of the cast and immersed in a 200 mM or 400 mM zinc sulfate solution to the crosslink the micelles via their surface-displaying metal-binding domains. The reaction was allowed to proceed to completion for 12-16 hours.

Micelle-Shedding.

The doubly crosslinked hydrogels were immersed in a known volume of 1× PBS (without zinc). The concentration gradient between the zinc inside the gel and the buffered solution surrounding it caused the diffusion of zinc into the PBS, thereby driving the micelles to dissociate from the hydrogel network and diffuse (or release) over time out of the covalently-crosslinked scaffold into the PBS bath. The amount of micelles released over time was measured by tracking the amount of released N-(1-Pyrenyl)maleimide into the PBS at specific time points (from 5 minutes to 96 hours) via spectrometry. N-(1-Pyrenyl)maleimide has a signature UV absorbance peak at 345 nm, which was used to trace the release of micelles and later to quantify the released mass using a calibration curve.

Microstructural Characterization.

Microstructures of hydrogels made from MF-ELP and NMF-ELP were evaluated by scanning electron microscopy (SEM), cryogenic transmission electron microscopy (cryo-TEM), and X-ray scattering. SEM was performed using a FEI XL30 SEM-FEG instrument with a beam density between 10 and 15 kV. The samples were prepared by freeze-drying the hydrogels for 48 hours and crushing them into small pieces to expose the internal surface of the hydrogel. The gel pieces were then sputter coated with gold and fixed on the SEM stage. Cryo-TEM imaging was performed on a FEI Tecnai $G^2$ Twin instrument and Gatan 626 cryogenic holder. The samples were vitrified using a FEI Mark III Vitrobot above 45° C. and 100% humidity. The crosslinker and polypeptide solution were sequentially and rapidly added to the grid, the solution was blotted for 5 seconds, plunged into liquid ethane, and transferred to the TEM instrument under liquid nitrogen. X-ray scattering data was collected using a SAXSLab instrument (Ganesha model) with a point collimated pinhole system and 2D configurable detector equipped with a Cu K-α X-ray source (wavelength, λ=0.15418 nm) operating at 50 kV. 40 µL of the gels confined between two Kapton films with thickness of about 1 mm was used. The measurements were made at source-to-detector distances of 1080, 480, and 180 mm at three different angles covering the wave vector range $0.1 < q < 10$ nm$^{-1}$. The 2D scattered intensity was monitored using a CCD detector and the 2D data was radially averaged using SAXSGUI software. Further analysis and data fitting was performed using SASfit software package. Each measurement was repeated at least three times. Hydrodynamic radius at different temperatures was measured using a temperature-controlled DLS instrument (DynaPro, Wyatt Technologies). A 90° detector measured intensity fluctuations from below to above the micellization temperature by increasing the temperature in increments of 2° C. $R_g$, $R_h$, and MW of the MF-ELP and NMF-ELP constructs were calculated using static light scattering data at different angles that were obtained from an ALV/LSE-5004 static light scattering instrument equipped with a CGS3 compact goniometer system. Measurements were performed on solutions of the ELPs at three different concentrations (25, 50, and 1000) at a temperature above the $T_{micelle}$ of the MF-ELP (about 41° C.).

Characterization of the Mechanical Properties of Hydrogels.

The mechanical and rheological properties of the hydrogels were studied using an Anton Paar rheometer with temperature control and a humidity chamber. The gels were loaded on 8 mm standard steel parallel plates or 25 mm diameter cone-plates and frequency sweep experiments were done from 0.1 to 100 Hz with a 1% strain limit. The compression and release of the MF gels were studied on a Micro Structure Analyzer (TA instrument). The gels were loaded on 8 mm standard steel parallel plates. The strain was changed with constant rate of 0.05 mm/s in positive and negative directions for compression and release tests.

Example 1

Molecular Design of MiGels

A recombinant peptide system having 2 components was designed to assemble into a hierarchical hydrogel. The first element was a peptide polymer of an elastin-like polypeptide (ELP). ELPs are a family of stimulus responsive peptide polymers consisting of repeats of the VPGXG peptide motif, in which the identity of amino acid, X, the molecular weight of the polymer,[39] and its architecture,[40] determine the temperature- and salt-dependent hydrophobicity of the polypeptide. ELPs exhibit lower critical solution temperature transition (LCST) behavior,[41] and the phase transition temperature of ELPs can be tuned by their composition and chain length[39] or by changing environmental conditions (such as ELP concentration and the type and concentration of the salt in and ELP solution).[39,42] ELPs are excellent candidates as building blocks for the design of hierarchical hydrogels because (i) they are genetically encodable, which allows enormous control in design, (ii) they express at high yields in bacterial hosts,[44b] and (iii) they can be purified easily by exploiting their LCST phase behavior[43] The latter two features enable gram scale quantities to be easily obtained, which is critical for the fabrication of hydrogels. Chilkoti and coworkers have extensively investigated peptide polymer ELPs that self-assemble into micelles,[44] providing a body of knowledge that can be used in the design of polypeptides as building blocks for the fabrication of micellar hydrogels.

Peptide polymer ELPs form micelles above a critical micellization temperature and are controlled by the hydrophobic portion composition.[44a] Herein, the constructs are referred to as micelle-forming (MF) ELPs. A MF-ELP was formed by fusing a relatively hydrophobic portion ((VPGVG; (SEQ ID NO: 1))$_{60}$) to a more hydrophilic portion ((VPGAGVPGGG; (SEQ ID NO: 2))$_{30}$). In some embodiments, the hydrophobic portion of the polymer can comprise 40-80 repeats of a VPGVG (SEQ ID NO: 1) peptide motif. In some embodiments, the hydrophilic portion of the peptide polymer comprises 10-50 repeats of a VPGAGVPGGG (SEQ ID NO: 2) peptide motif.

An ELP that has a similar composition and chain length as the MF-ELP, but where the amino acids are not arranged in a peptide polymer architecture (termed the non-micelle-forming ELP (NMF-ELP) was also synthesized as a negative control for the effect of micellization on network assembly. The NMF-ELP had the sequence (VPGAGVPGGG; (SEQ ID NO: 2))$_{60}$.

Figure 9A:
FIG. 9A is a representation of one sequence of non-micelle forming elastin-like polypeptide that can be used in accordance with some embodiments of the presently disclosed subject matter.
Figure 9B:
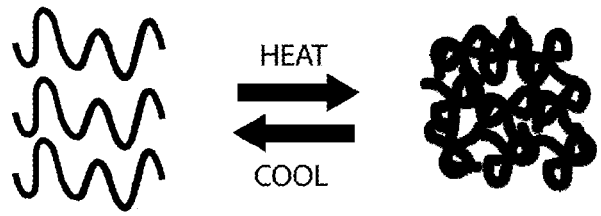
FIG. 9B is a schematic diagram of reversible temperature-triggered aggregation and dissociation of the polypeptides of FIG. 9A into large particles.

The second design element in the recombinant peptide used to form hierarchical hydrogels was a transition metal-binding peptide presented at the hydrophilic terminus of the MF-ELP (FIG. 4A) and the NMF-ELP (FIG. 9). A peptide with an amino acid sequence (HEDGHWDGSEHGY (SEQ ID NO: 3)) taken from the consensus zinc-binding sequence found in the active sites of matrix metalloproteinases was selected.[45],[46] Although many transition metal binding peptides were available, a peptide that bound $Zn^{2+}$ was selected because (in contrast to $Ni^{2+}$ and $Cu^{2+}$), $Zn^{2+}$ is significantly less toxic, with a physiological concentration of 20 µM[47] and a maximum tolerated concentration of 200 µM in systemic circulation.[48]

Figure 4A:
FIG. 4A is a representation of an amino acid sequence of micelle-forming elastic-like polypeptide in accordance with some embodiments of the presently disclosed subject matter.
Figure 4B:
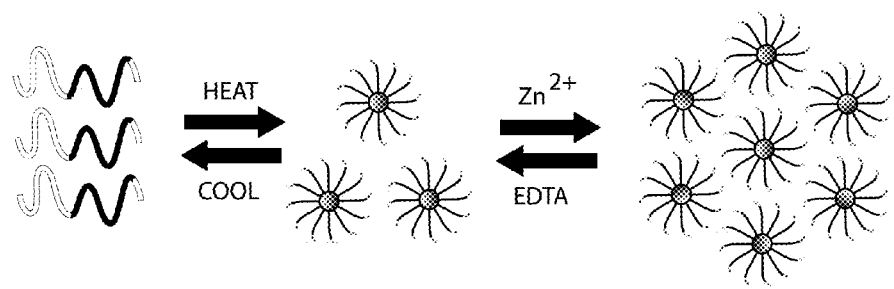
FIG. 4B is a schematic of temperature-triggered micellization of peptide polymers, assembly of the micelles into a stabilized network by addition of metal ions, and disassembly of the network by the addition of chelant.
Figure 4C:
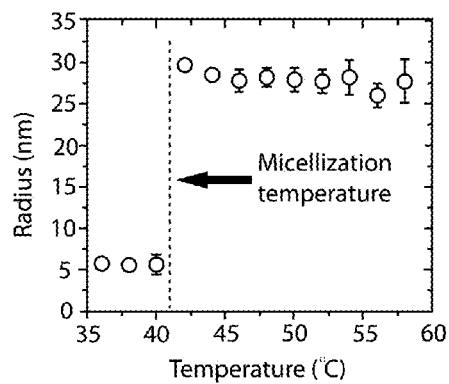
FIG. 4C is a graph of hydrodynamic radius of micelle-forming elastic-like polypeptide as a function of solution temperature, measured by DLS.
Figure 4D:
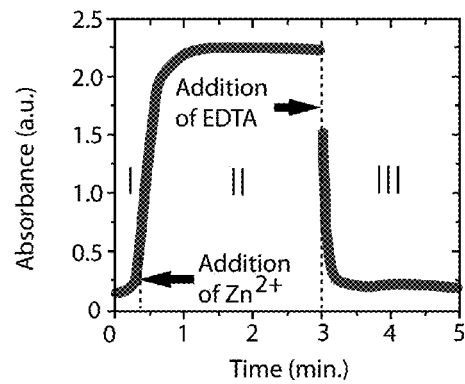
FIG. 4D is a graph of the optical density of a solution of micelle-forming elastic-like polypeptide as a function of time.
Figure 19:
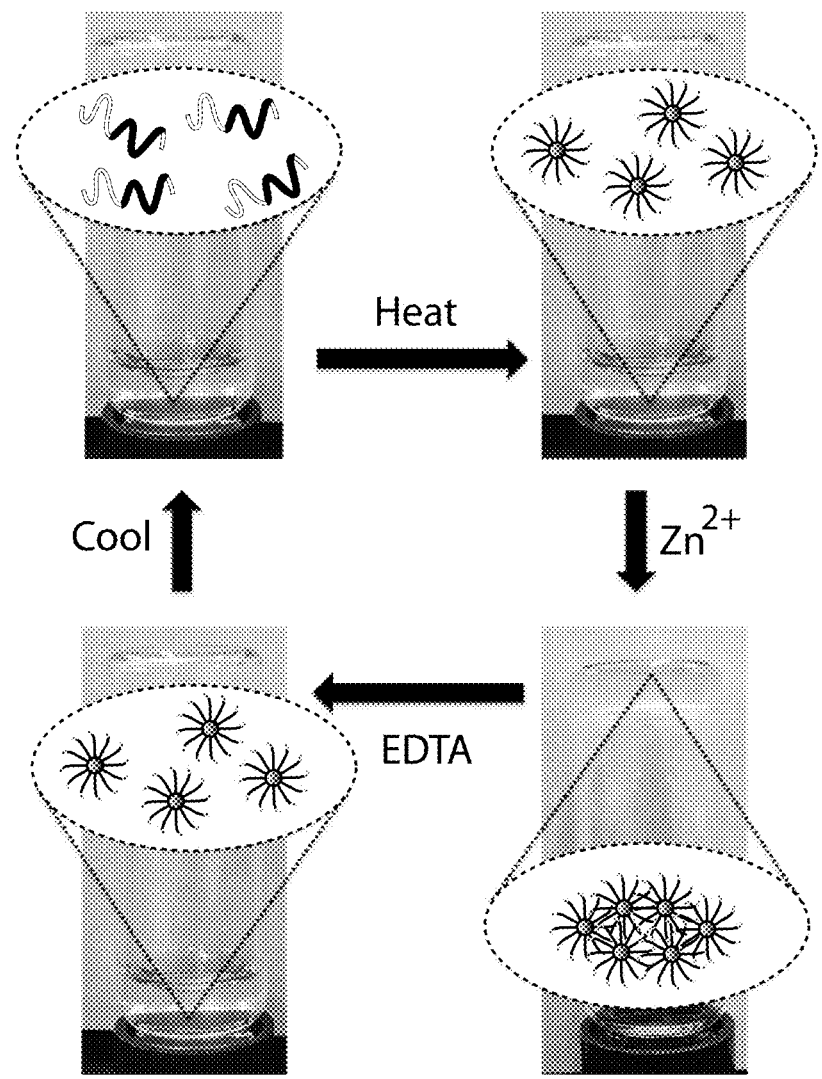
FIG. 19 is a schematic illustrating the formation of MiGels in accordance with some embodiments of the presently disclosed subject matter.

FIG. 4A illustrates the amino acid sequence of the MF-ELP. FIGS. 4B and 19 are schematics of temperature-triggered micellization of the peptide polymer ELPs, metal-directed assembly of the micelles into a metal coordination stabilized network by addition of zinc ions, and disassembly of the network by the addition of EDTA. FIG. 4C illustrates hydrodynamic radius ($R_h$) of the MF-ELP (100 µM, 0.5% w/v) as a function of solution temperature, measured by DLS. FIG. 4D shows optical density at 350 nm of a solution of MF-ELP (100 µM at 40° C.) indicating micelles (region I), network formation by addition of $Zn^{2+}$ (region II), and disassembly back into micelles upon addition of EDTA (region III).

Example 2

Micelle Assembly and on-Demand Network Formation/Dissolution

FIG. 4B is a schema that depicts micelle formation, network formation from micelles upon addition of $Zn^{2+}$, and network disaggregation back into micelles upon chelation of the $Zn^{2+}$ ions. The MF-ELP and NMF-ELP was characterized in a dilute aqueous solution (100 µM, 0.5% w/v) and in the presence of $Zn^{2+}$. Below the micellization temperature ($T_{micelle}$), the MF-ELP was not sufficiently amphiphilic to undergo self-assembly. Above the $T_{micelle}$, the preferential desolvation of the more hydrophobic portion relative to the more hydrophilic portion imparted sufficient amphiphilicity to drive self-assembly of the MF-ELP into micelles. The temperature-triggered assembly of the MF-ELP into micelles was confirmed by dynamic light scattering (DLS) (FIG. 4C). The hydrodynamic radius ($R_h$) of the MF-ELP below its $T_{micelle}$ of about 41° C. was about 5 nm, which was consistent with other reports for random coil polypeptides.[49] Above the $T_{micelle}$ of the MF-ELP, the $R_h$ of the MF-ELP also increased to about 25-30 nm, which was also consistent with previous reports of micelles consisting of ELP peptide polymers.[44a,49c, 50] In contrast, the NMF-ELP formed large particles (>1 µm) as the temperature was raised above about 40° C. (FIG. 10).

Addition of $Zn^{2+}$ ions resulted in the crosslinking of the micelles formed from 100 µM (0.5% w/v) MF-ELP into large gel particles. Solutions containing these aggregates had a significantly higher optical density compared to solutions of non-aggregated micellar particles (FIG. 4D). Micelle aggregation can be reversed by adding a chelating agent such as ethylenediaminetetraacetic acid (EDTA) due to its high affinity for zinc ions. Addition of EDTA to a solution of aggregated micelles at temperatures above the micellization temperature resulted in a rapid drop in the solution optical density to its pre-aggregation level, which suggested disaggregation to the original discrete micellar state (FIG. 4D).

Example 3

Characterization of Micelles by Light Scattering

Figure 11:
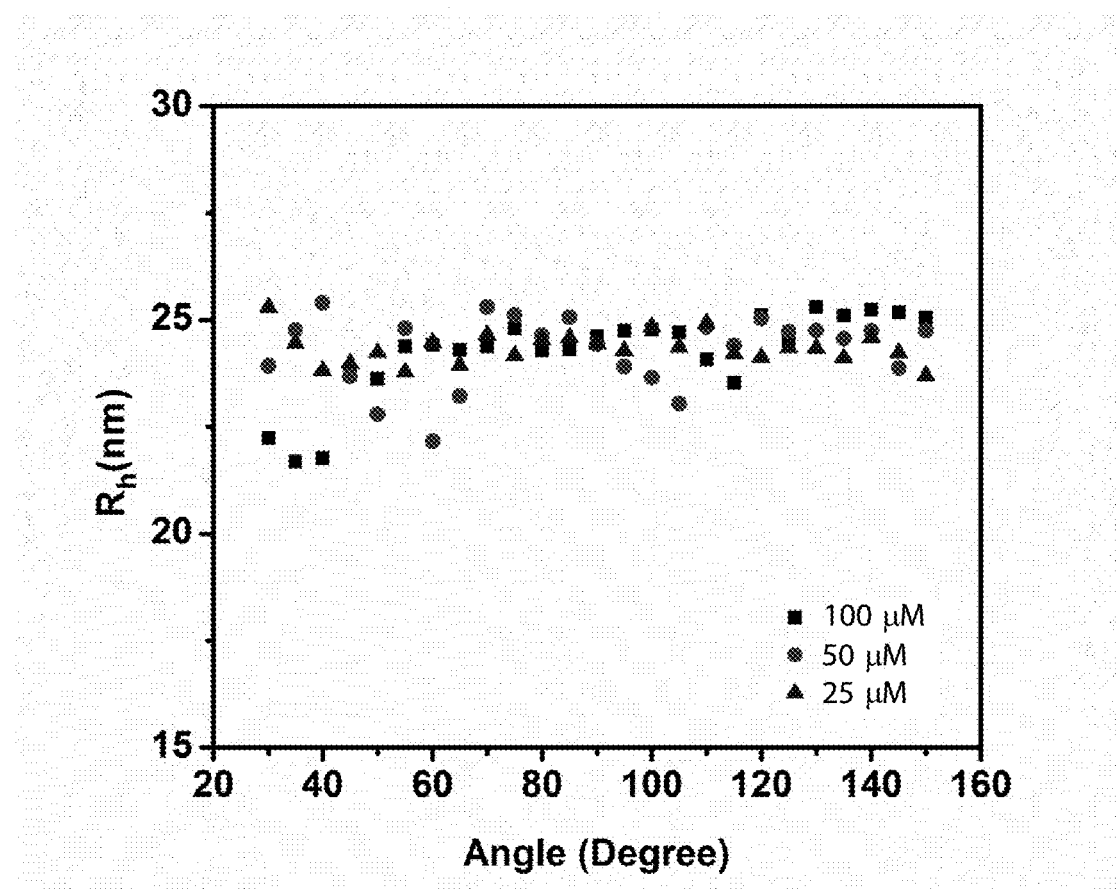
FIG. 11 is a graph of the hydrodynamic radius as a function of angle (degree) of non-micelle forming elastin-like polypeptide in water.

To further investigate the size, shape and aggregation number of the micelles formed from the MF-ELP, the self-assembled nanostructures formed from MF-ELP by DLS and static light scattering (SLS) were examined at different angles at a solution temperature above the $T_{micelle}$. At three different concentrations (25, 50, and 100 µM, i.e., 0.125, 0.25 and 0.5% w/v), the MF-ELP formed micelles with a $R_h$ of about 23 nm as measured by DLS at angles ranging from 30° to 150° (FIG. 11, measuring DLP of MF-ELP in water, triangle=25 uM, circle=50 uM, and square=100 uM; Table 1). The relatively constant size of the micelles measured at different angles suggested a spherical shape.[51]

Figure 12:
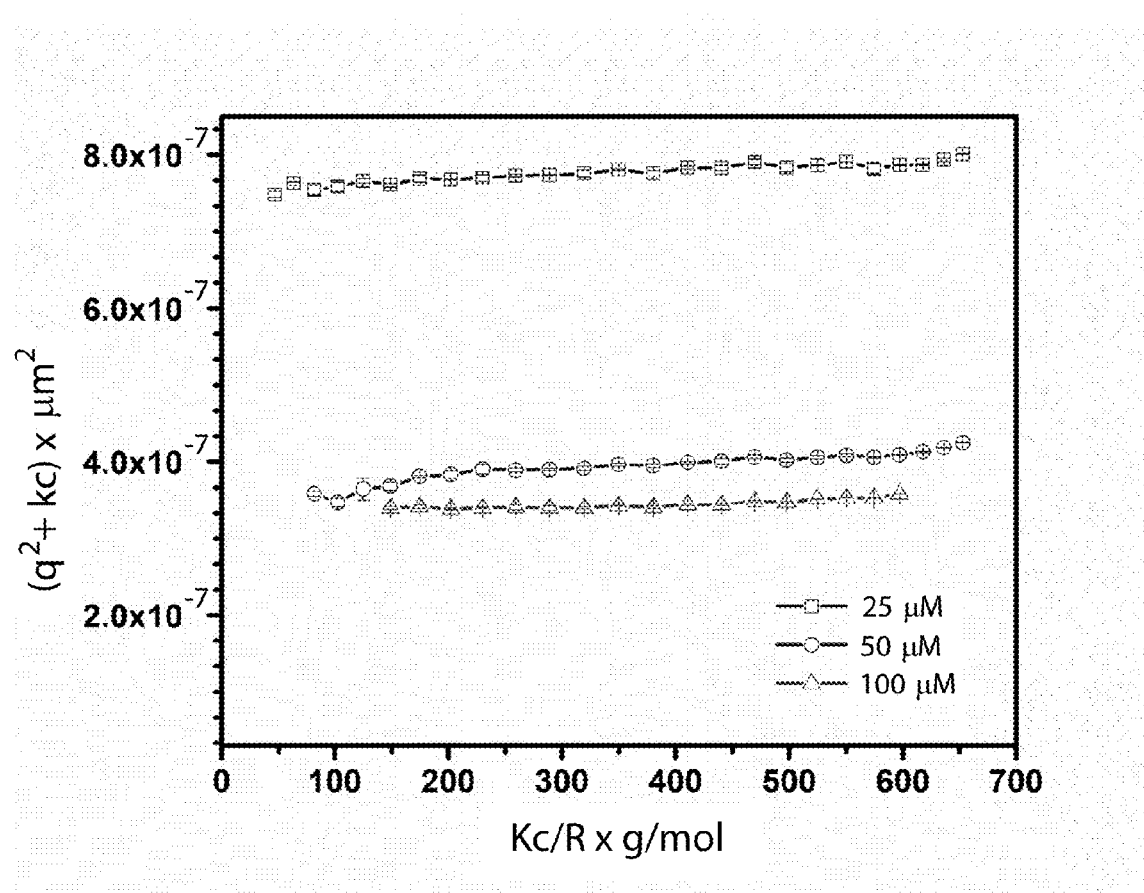
FIG. 12 is a graph of the static light scattering of non-micelle forming elastin-like polypeptide at differing concentrations.

SLS measurements were also conducted to measure the radius of gyration ($R_g$) and molecular weight ($M_w$) of the micelles formed at the three different concentrations (FIG. 12, squares=25 uM, triangles=50 uM, and diamonds=100 uM, q is the scattering vector, k is an arbitrary constant, K is optical contrast, R is the Rayleigh constant, and c is concentration; Table 1). The radii of gyration of the micelles measured at these concentrations ranged from 15 to 22 nm (Table 1), which was slightly smaller than $R_h$, as expected for spherical particles.[51-52] The ratio of $R_g$ to $R_h$ for different concentrations ranged from 0.72 to 0.79 which also suggested the existence of "hard spheres" in solution.[42] As the MF-ELP was monodisperse with a molecular weight of 48.6 KDa, the average number of the polypeptide chains in each micelle (i.e., the aggregation number) was estimated. The aggregation number was corrected for the amount of water trapped in the micelles by considering the water content of each micelle to be similar to that in ELP coacervates (determined to be roughly 60% of the coacervate volume).[21] Using this assumption, the number of chains in each micelle was estimated to be about 20, which also corresponded to the number of crosslinking motifs displayed on the surface of a single micelle.

TABLE 1

$R_h$, $R_g$, $M_w$, Aggregation Number of Micelles Formed at 25 μM, 50 μM, and 100 μM ELP

| | Concentration (μM) | | |
|---|---|---|---|
| | 25 | 50 | 100 |
| $R_h$ (nm) | 22 | 24 | 24 |
| | (±3.3%) | (±3.4%) | (±1.5%) |
| $R_g$ (nm) | 16 | 19 | 18 |
| | (±3.6%) | (±4.4%) | (±6.3%) |
| $M_w$ (g/mol) | 1.325 × 10⁶ | 2.794 × 10⁶ | 3.021 × 10⁶ |
| | (±0.2%) | (±1.0%) | (±0.6%) |
| Aggregation number | 15 | 23 | 25 |

Hydrodynamic radius ($R_h$ from DLS) and molecular weight ($M_w$), radius of gyration ($R_g$) and micelle aggregation number (from SLS) of micelles formed from MF-ELP for three different concentrations at 42° C.

Example 4

Formation of MiGels

Hydrogels were constructed containing 5, 10, and 15% w/v MF-ELP by adding zinc sulfate to a polypeptide solution, resulting in a 7.5 to 1 molar ratio of $Zn^{2+}$ ions to peptide binding sites. The temperature of the polypeptide solutions was kept at 45° C. (above the micellization temperature of the MF-ELP, but below the transition temperature for bulk aggregation) to ensure micelle formation before crosslinking. Addition of zinc sulfate to the solution of the MF-ELP resulted in rapid formation of a gel (FIG. 5A, showing images of MF-ELP 10% w/v in micellar suspension before crosslinking on left and after crosslinking with 20 mM zinc sulfate on right to form hydrogel). The hydrogels were maintained at the same temperature for several hours to allow complete crosslinking and were subsequently centrifuged briefly to remove air bubbles before characterization.

After crosslinking, the hydrogels were stable at room temperature, which was below the $T_{micelle}$ of about 41° C. The stability likely resulted from a decrease in the $T_{micelle}$ in the presence of zinc sulfate such that the micelles were stable at room temperature.g To test the hypothesis, zinc sulfate (or sodium sulfate) was added to MF-ELP at room temperature and an increase in optical density characteristic of the formation of micelles was observed (FIG. 13, a graph of optical density as a function of time, showing micelle formation in a 10% w/v solution of MF-ELP at 25° C. upon addition of 20 mM $ZnSO_4$ (top line) or $Na_2SO_4$ (lower line); arrows show the time at which the salts were added).

For solutions of NMF-ELP, the optical density profile as a function of temperature did not change appreciably in the presence of monovalent ($Na^+$) of divalent ($Zn^{2+}$) metal ions (FIG. 10A, left line represents no salt, middle line represents 2 mM $ZnSO_4$, and right line represents 2 mM $Na_2SO_4$). DLS of the NMF-ELP also showed that the presence of $Zn^{2+}$ ions had little impact on the size of the aggregates as a function of temperature compared to the same ELP in water (FIG. 10B, squares=2 mM $ZnSO_4$, circles=no salt). Further, addition of zinc sulfate to solutions of NMF-ELP above the transition temperature (about 40° C.) resulted in the formation of a typical ELP coacervate that did not show gel-like properties (FIG. 16), indicating that the presence of ELP micelles were necessary for the formation of a percolated crosslinked network.

Example 5

Characterization of MiGels with Electron Microscopy

The microstructure of the hydrogels was examined by cryogenic transmission electron microscopy (cryo-TEM) and scanning electron microscopy (SEM). Using cryo-TEM the initial stage of the gel formation process (10 seconds after addition of $ZnSO_4$) was captured in a dilute (1% w/v polypeptide) solution (FIG. 5B, a cryo-TEM of the incipient network 1% w/v MF solution frozen 10 seconds after addition of 2 mM $ZnSO_4$). Cryo-TEM samples were more dilute than those typically used to form the MiGels 5 wt %) to enable visualization of the incipient network before crowding of the micelles; the molar ratio of crosslinker ($Zn^{2+}$) to MF-ELP was kept the same as that used to form MiGels at the higher concentrations.

Figure 14A:
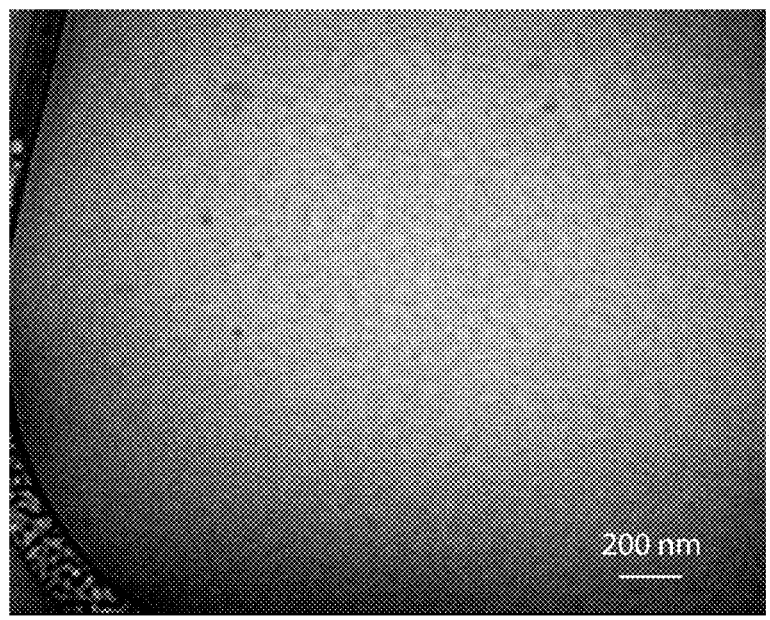
FIG. 14A is a cryo-electron microscopy image of non-micelle forming elastin-like polypeptide vitrified.
Figure 14B:
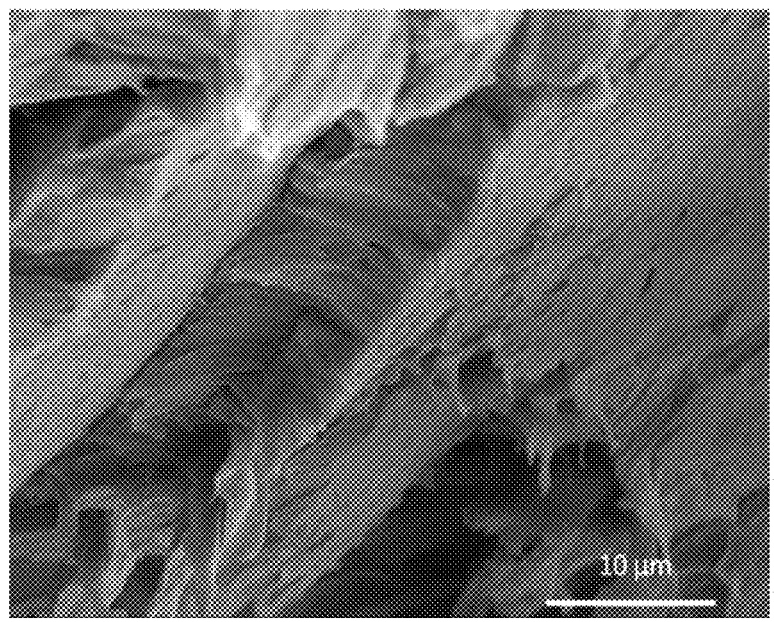
FIG. 14B is a scanning electron microscope image of freeze dried non-micelle forming elastin-like polypeptide coacervate.

During the early stages of network formation, cryo-TEM micrographs revealed individual micelle-like particles (i.e., of size comparable to that measured by light scattering) that were interconnected in a web-like network, which was in clear contrast with cryo-TEM micrographs of NMF-ELPs at a similar stage after addition of zinc ions (no such network was evident) (FIG. 14A, cryo-TEM of coacervate 1% w/v NMF-ELP solution vitrified 10 seconds after addition of 2 mM $ZnSO_4$ at 45° C.; FIG. 14B, SEM of a 10% w/v NMF-ELP coacervate freeze-dried 12 hours after the addition of 20 mM $ZnSO_4$ at 45° C.).

SEM of freeze-dried 10% w/v MiGels after maturation of the crosslinked network (12 hours after addition of $ZnSO_4$) showed a porous internal structure with a pore size less than 10 μm (FIG. 5C), which was in clear contrast with the SEM images of the corresponding NMF-ELP structures (FIGS. 14A and 14B) that did not show a similar porous structure, suggesting that the crosslinking of micelles was related to the development of macroporosity.

Together, cryo-TEM and SEM analyses demonstrated a fundamental difference in microstructure of the hydrated MF-ELP-based and NMF-ELP-based materials. The formation of relatively large pores observed in the MF-ELP hydrogels was believed to be a result of the crosslinking of intact micellar structures. In contrast, the NMF-ELP lacked the ability to form a well-defined hybrid network that included both (i) crosslinks formed by hydrophobic and van der Waals interactions and (ii) crosslinks formed by the coordination of $Zn^{2+}$, and thus did not yield a hydrogel, but formed a highly entangled coacervate above the transition temperature.

Example 6

Characterization of MiGels with X-Ray Scattering

Figure 6:
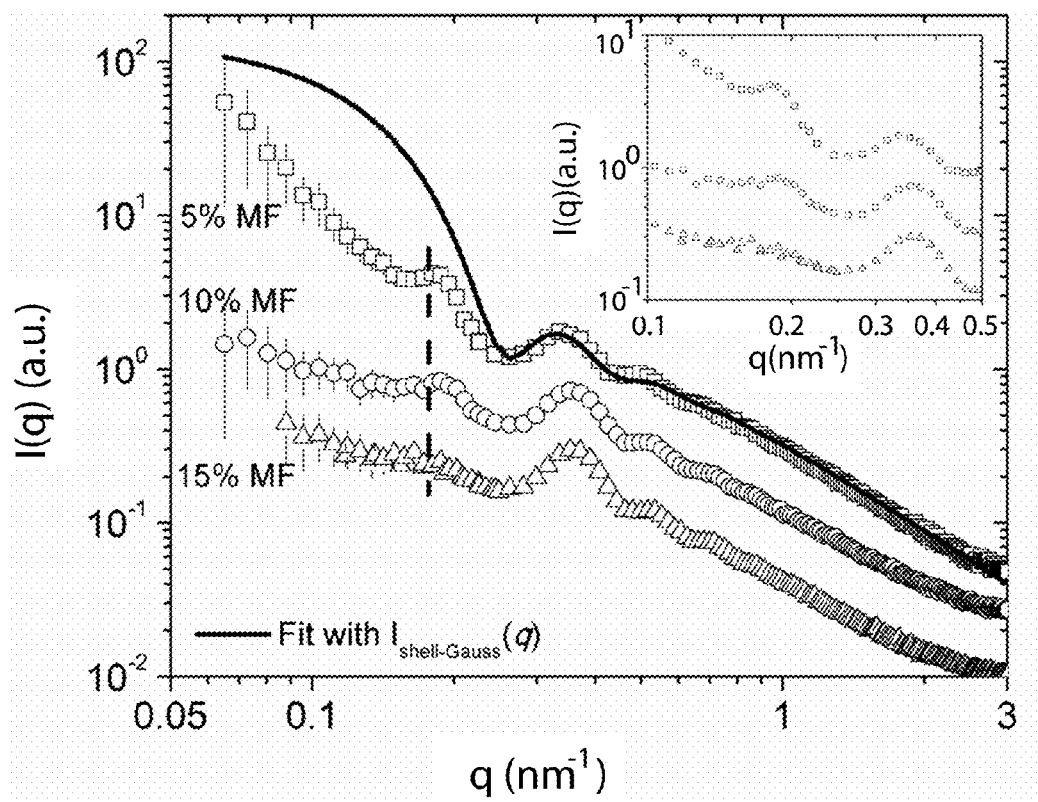
FIG. 6 is a small angle x-ray scattering intensity profile of MiGels formed at three different concentrations of micelle-forming elastic-like polypeptide in accordance with some embodiments of the presently disclosed subject matter.

FIG. 6 shows the small angle X-ray scattering (SAXS) profiles for three different MiGels formed at different concentrations of MF-ELP (squares=5% w/v MiGel; circles=10% w/v MiGel; triangles=15% w/v MiGel; the data is offset for clarity of presentation). The solid black line of FIG. 6 represents the fit to 5% v/v MiGel SAXS profile at $q>0.3$ $nm^{-1}$ using the form factor of spherical shells and Gaussian chains ($I_{shell-gauss}$). The dashed line is a reference to indicate the interparticle correlation peak for 3 gel concentrations (also shown in the inset).

Figure 15:
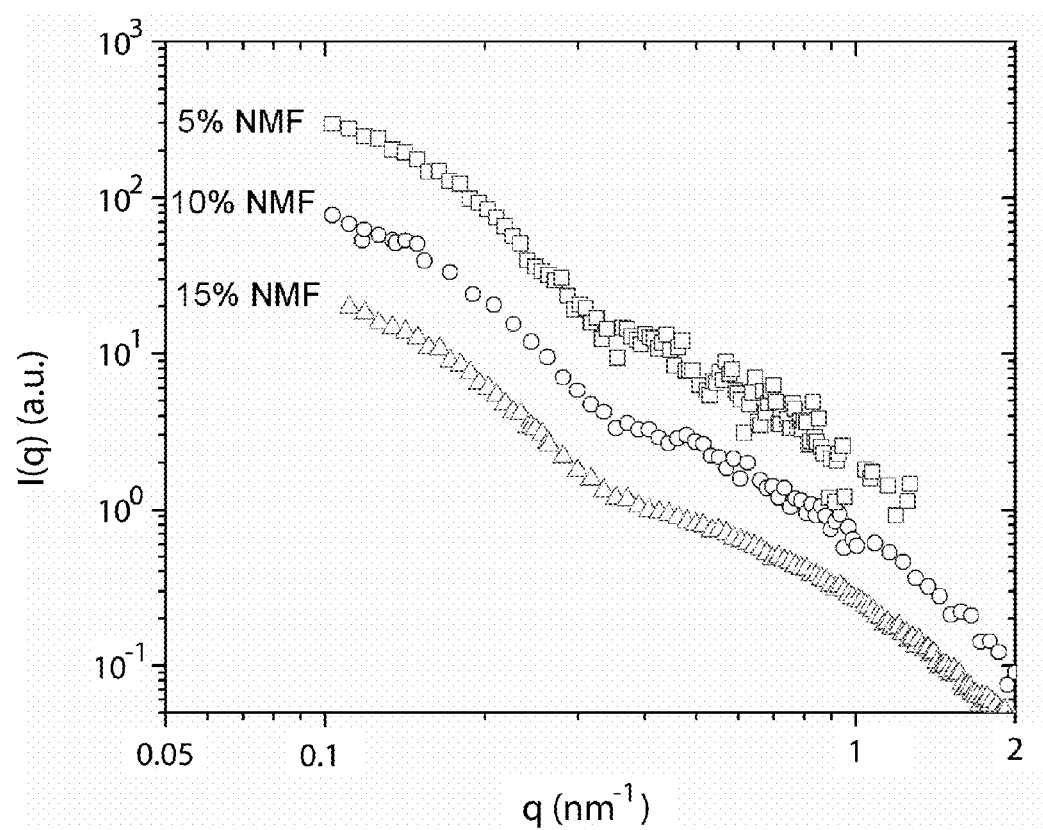
FIG. 15 is a small angle x-ray scattering intensity profile of non-micelle forming elastin-like polypeptide coacervate formed from 3 different concentrations of non-micelle forming elastin-like polypeptide.

The scattering intensity 1(q) is presented as a function of wave vector $q=(4\pi/\lambda)\sin\theta$, where $\lambda=0.15418$ nm and $2\theta$ is the scattering angle. At $q>0.5$ $nm^{-1}$, the SAXS profiles show $I(q) \propto q^{-2}$ dependency of scattering intensity, which is characteristic of polymer Gaussian chains. Modeling of the X-ray scattering data for the 5% w/v MiGel was carried out as described herein (see Table 2 for fitting parameters). In FIG. 6, the discrete points are the experimental SAXS data and the solid line is the fit to the curve using a spherical core-shell model. Scattering in the high q region, i.e., $q>0.2$ $nm^{-1}$, reflected the signature of the size and shape of the self-assembled micelles in the hydrogel and was well represented by the core-shell form factor. The position of the form factor primary maxima ($q=0.3$ $nm^{-1}$) did not change appreciably upon increasing the concentration of MF-ELP from 5% w/v to 15% w/v (FIG. 6), indicating that the local geometry and structure of micelles in the hydrogels remained unaltered upon change in concentration. Core micelle radii of about 15 nm were obtained for all MiGels examined, and were in reasonable agreement with the results of light scattering. No form-factor oscillation was observed for samples of NMF-ELP. (FIG. 15, which shows SAXS intensity profiles for NMF-ELP coacervate formed at 45° C. from 3 different concentrations of NMF-ELP. Data were taken after the addition of 10 mM $ZnSO_4$; squares=5% w/v; circles=10% w/v; triangles=15% w/v; the data has been offset for clarity of presentation).

The core-shell form factor model did not reproduce the maxima at q of about 0.18 $nm^{-1}$ observed for the MiGels (FIG. 6). The peak was believed to correspond to the spatial correlations between the micelles in the hydrogel phase. Direct fitting of the pseudo-order (or structure factor) peak was non-trivial. However, the correlation distance 'D' between the micelles can be extracted from the location of peak maxima '$q_c$' using the relation: $D=2\pi/q_c$.[53] Table 3 summarizes the correlation distances between the micelles obtained for the three different polymer concentrations. The peak shifts to higher q values with increasing concentration (FIG. 6 inset) corresponded to a decrease in the correlation distance for the micelles from 35 nm to 24 nm. For the studied gel concentrations, it was discovered that the distance scales as $D \propto conc.^{1/3}$ (Table 1).

TABLE 2

Summary of the Parameters Used to Fit the X-Ray Scattering Data for 5% w/v MiGels

| $\rho_{core}$ ($cm^{-2}$) | $x_R$ | $x_{R+dR}$ | dR (nm) | R (nm) | $R_g$ (nm) | $I_0$ |
|---|---|---|---|---|---|---|
| $1.32 \times 10^{-4}$ | 0.6 | 0.95 | 5.3 | 15.7 | 2.7 | 2.5 |

TABLE 3

Correlation distance (D) between the micelles in MiGels

| Concentration (c) of polypeptide in MiGel (% w/v) | $q_c$ ($nm^{-1}$) | D (nm) | $r_D = D/D_5$ | $r_c = c^{1/3}/c_5^{1/3}$ |
|---|---|---|---|---|
| 5 | 0.18 | 34.9 | 1.0 | 1.0 |
| 10 | 0.20 | 31.4 | 1.1 | 1.2 |
| 15 | 0.26 | 24.1 | 1.4 | 1.4 |

The scattering curve for a 5% w/v MiGel showed a steep increase in the scattering intensity at low q, which can be attributed to the interlinking of the micelles into larger structures.[13] However, the increase in intensity became less pronounced with increasing polymer concentration. It was not possible using X-ray scattering alone to determine the exact origin of the behavior. However, two effects were believed to contribute to the decrease in scattering intensity at higher concentrations of MF-ELP.

First, increasing concentration may lead to crosslinking of the micelles into denser networks and hence the scattering interface may become more diffuse. Second, the increase in polypeptide and $Zn^{2+}$ concentrations can change the effective scattering length density of the interlinked Gaussian chains and the surrounding aqueous media. Similar effects have been observed by contrast variation in small angle neutron scattering experiments (SANS) for peptide polymer micelles.[54]

In summary, microstructural characterization with SAXS provided further evidence that hydrogels formed from MF-ELP comprise networks of intact, randomly packed micelles with spherical cores. This observation is in accordance with the theory of random packing of spheres, where the mean inter-particle pair distance scales similarly.[55]

Example 7

Rheological Studies of Micelles

Figure 13:
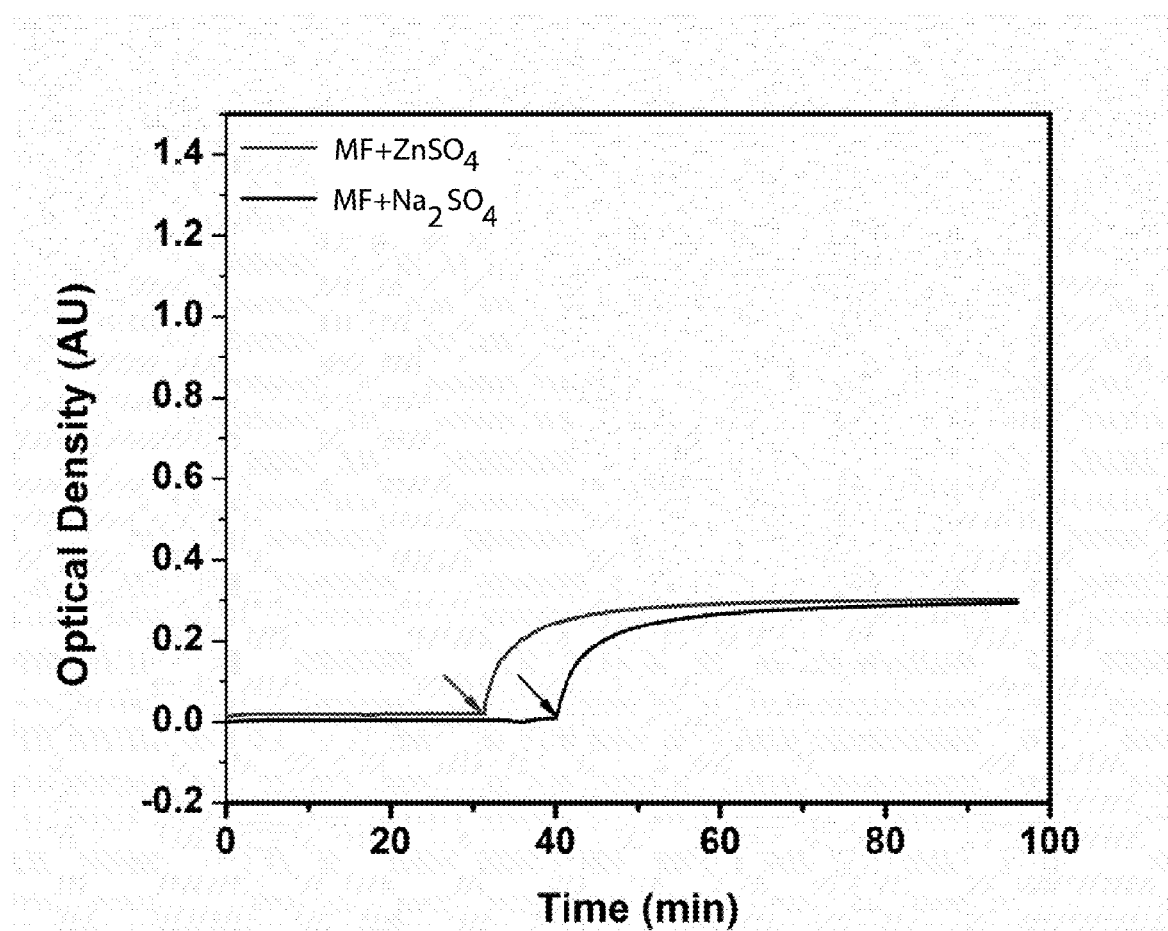
FIG. 13 is a graph of optical density as a function of time of a solution of non-micelle forming elastin-like polypeptide upon the addition of salt.
Figure 16:
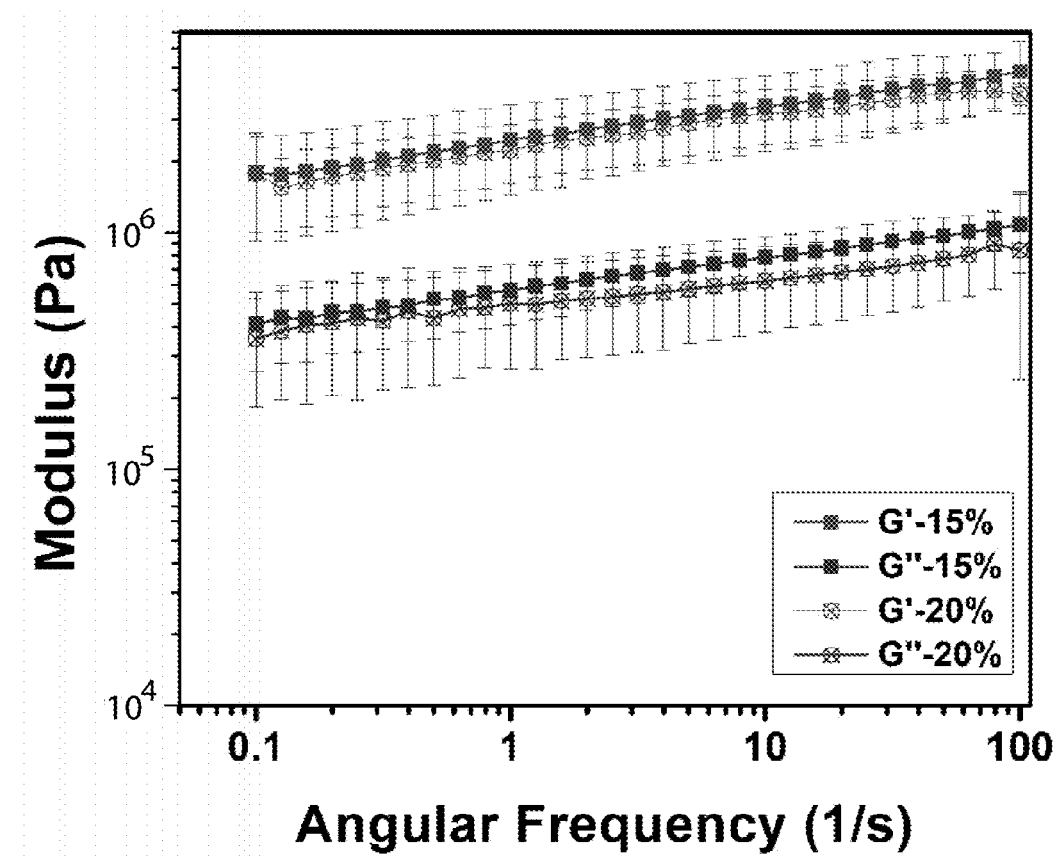
FIG. 16 is a graph of storage and loss modulus of MiGels constructed from micelle forming elastin-like polypeptide as a function of angular frequency.

The rheological behavior of MiGels was studied at different concentrations of the MF-ELP (FIGS. 7A, 16) and at 25° C., above $T_{micelle}$ at the concentrations of $ZnSO_4$ used (see FIG. 13). It was hypothesized that forming networks with different crosslink densities lead to the ability to tune the mechanical properties of MiGels. FIG. 7A illustrates storage and loss modulus for MiGels at 25° C. for 10% w/v and 5% w/v polymer concentrations; each point on the plot is an average value of 3 independent measurements and error bars are calculated standard deviations of the 3 measurements (filled squares and filled circles=10% concentration; open squares and open circles=5% concentration). FIG. 16 is a graph of modulus as a function of angular frequency; storage (upper points) and loss (lower points) moduli of 15% w/v and 20% w/v MiGels made by incubation of MF-ELP with 30 mM and 40 mM $ZnSO_4$ respectively for 12 hours at 45° C.; each point on the plot is an average value of 3 independent measurements and error bars are calculated standard deviations of the 3 measurements).

For MiGels formed from MF-ELP concentrations >5% (i.e., 10, 15, and 20% w/v), the storage and loss moduli were relatively independent of the angular frequency in a range from 0.1 to 100 s$^{-1}$ (see FIG. 7A for data for 10% w/v). The hydrogels were viscoelastic materials that exhibited storage moduli one order of magnitude higher than the corresponding loss moduli. The storage moduli for the MiGels constructed from 10, 15 and 20% w/v MF-ELP were all about 1 MPa, considerably higher than reported storage moduli of other non-covalently crosslinked hydrogels with similar polymer concentrations, including micellar hydrogels.[16, 24, 56] The storage modulus for 5% w/v hydrogels was about an order of magnitude less than that of the 10-20% w/v hydrogels, indicating that tuning the moduli of the MiGels was possible by changing the MF-ELP concentration below 10% w/v.

The relatively high moduli of the MiGels may be due to a combination of structural factors, each of which individually has been shown to be effective in enhancing mechanical properties of micellar hydrogels. The hierarchical microstructure of the hydrogel may provide for especially efficient crosslinking[57]. The concentration of active stress-bearing sub-chains, derived from the kinetic theory of rubber elasticity is greater than the concentration of peptide strands. In other words, an untangled polymer network of unit efficient crosslinking per se would not result in such a high modulus.[58] The hydrophobic cores of the micelles are aggregates of large hydrophobic polypeptide chains within a minimal solution fraction, and it is possible that these aggregates can essentially function as highly entangled nodes throughout the gel. These micellar cores could function as especially stiff components that contribute considerably to the high modulus of the gels.[58] It is further notable that the MiGels are highly porous (FIG. 5C, showing SEM of a freeze-dried mature MiGel, 10% w/v MF-ELP, 20 mM ZnSO$_4$), with pore sizes much larger than the hydrodynamic radii of the micelles. Also, fibrillar structures made from individual micelles are evident from cryo-TEM images of the incipient MiGel network (FIG. 5B), suggesting that the gels are not comprised merely of agglomerations of micelles, but rather of filamentous structures of tightly connected micelles that form a network superstructure. Such filamentous structure has been observed for ELP micelles before.[29] It has also been shown that hydrogels made of micelle-based filaments can show enhanced mechanical properties depending on their core size.[59] Efficient and perhaps synergistic combination of hydrophobic interactions and coordination chemistry, both of which have been shown to be effective in enhancing the mechanical characteristics of hydrogels, is likely key to imbuing the MiGels with mechanical robustness despite the lack of covalent crosslinking.[23, 60] [24]

Figure 17:
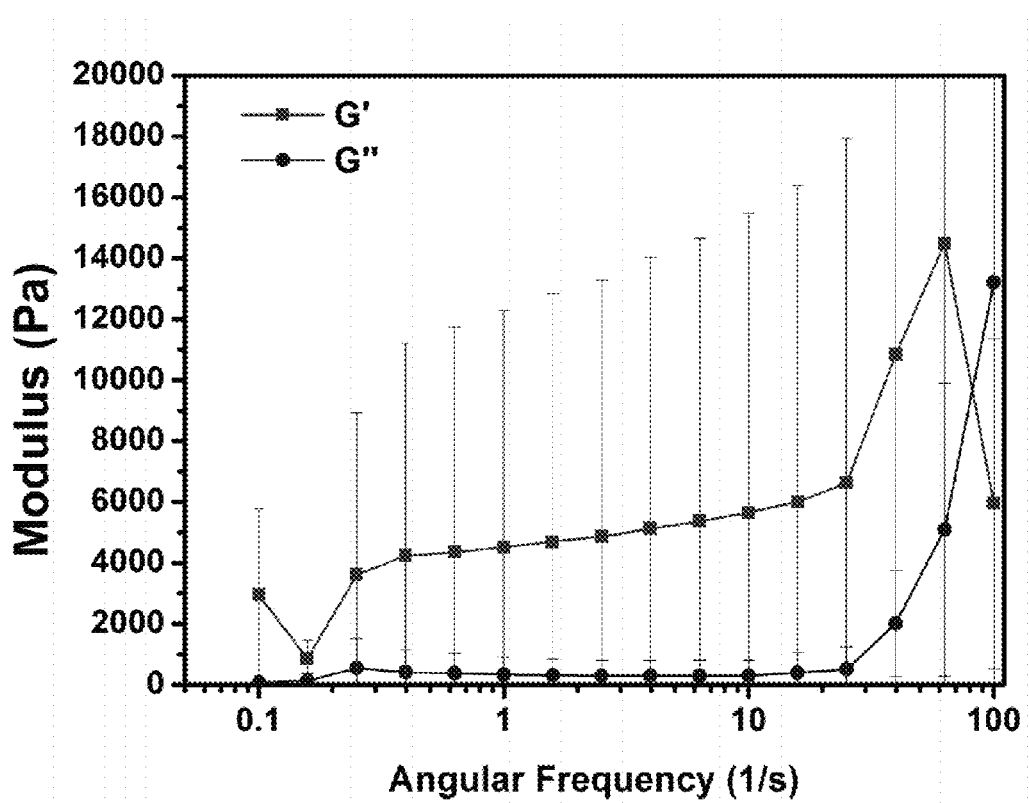
FIG. 17 is a graph of the storage and loss modulus of non-micelle forming elastin-like polypeptide coacervates as a function of angular frequency.

In contrast, addition of ZnSO$_4$ to NMF-ELP resulted in the formation of materials with characteristics of a fluid with low moduli (FIG. 17, a graph of modulus as a function of angular frequency; storage and loss moduli of 10% w/v NMF-ELP coacervates formed by the addition of 20 mM Zn$^{+2}$ to polypeptide solutions at 45° C., the solutions were kept at 45° C. for 24 hours before experimentation). The results are likely due to the fact that, in contrast to the MF-ELP that can form network associations (i.e., crosslinks) by both ion coordination and formation of micellar cores, the NMF-ELP only has one crosslinkable group and thus did not form a gel network.

Example 8

Compression Tests of the MiGels

Figure 18:
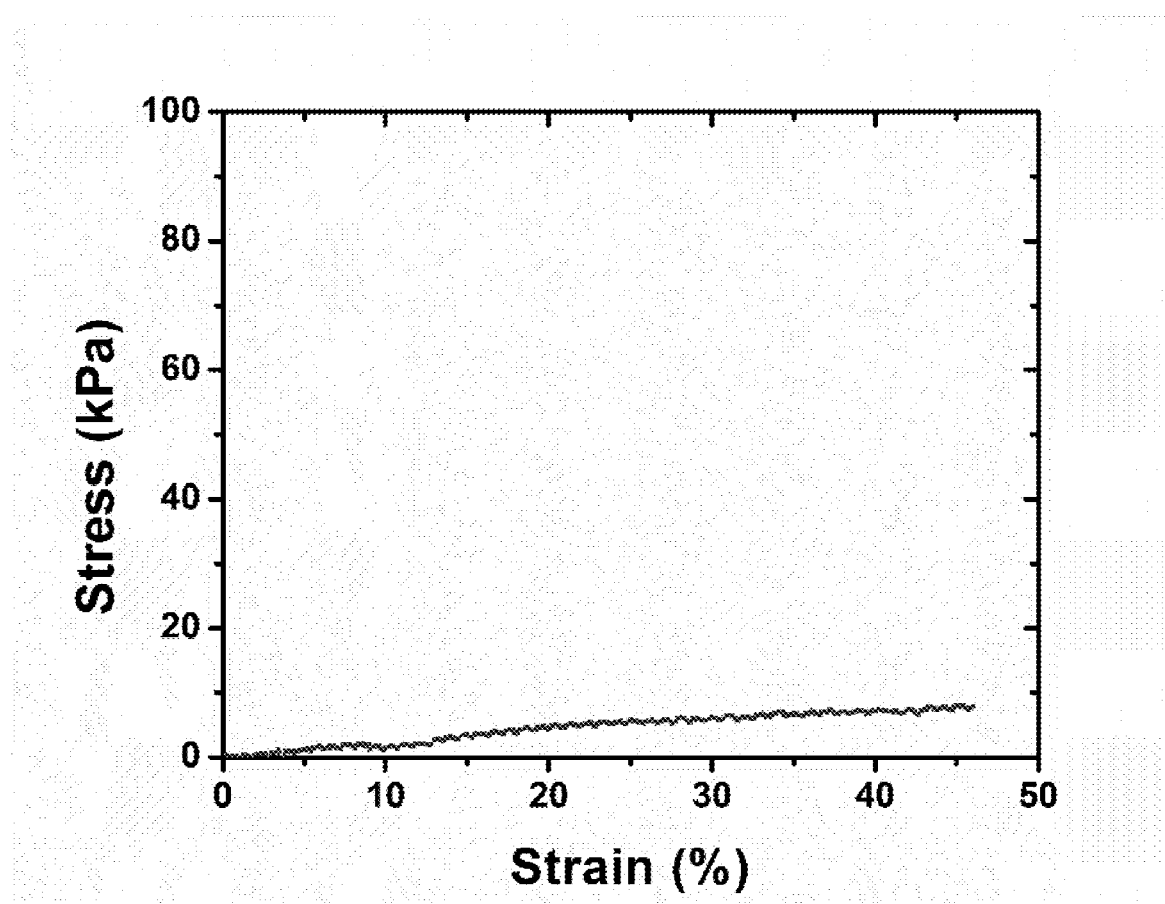
FIG. 18 is a compressive stress-strain curve for non-micelle forming elastin-like polypeptide coacervate.

Unconfined compression tests were conducted on MiGels formed from a 10% w/v solution of the MF-ELP. The gels were cast into disks, and each disk was compressed to prescribed strains and then unloaded for two cycles. The gels underwent significant deformation during the compression tests (FIG. 7B, a graph of stress (MPa) as a function of % strain; cyclic compression and expansion test for 10% w/v MiGels at 25° C. from 0-55% (solid line) and then immediately from 25% to 75% compressive strain (dashed line)). Upon unloading, large hysteresis loops were observed in the stress vs. strain curves of the gels, indicating significant energy dissipation due to the breaking and subsequent at least partial reformation of reversible crosslinks. From the initial slope of the stress-strain curve, the maximum compressive moduli of the MiGels was calculated, which was as high as about 0.8-1.0 MPa. The compressive modulus was much higher than that of the NMF-ELP control (FIG. 18, a compressive stress-strain curve for 10% w/v NMF-ELP coacervate after incubation with 20 mM ZnSO$_4$ for 6 hours at 45° C.) and other biopolymer-based hydrogels.[20a] [60b]

Example 9

Self-Healing Properties of MiGels

Figure 8A:
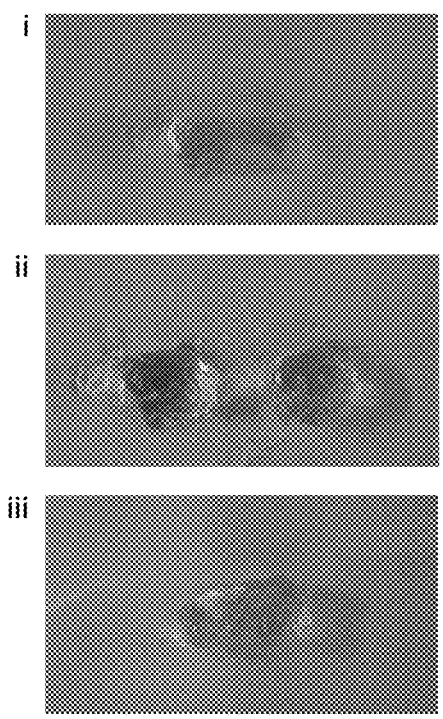
FIG. 8A is an image of a self-healing MiGel in accordance with some embodiments of the presently disclosed subject matter prior to severing (i), after severing (ii), and after self-healing (iii).
Figure 8B:
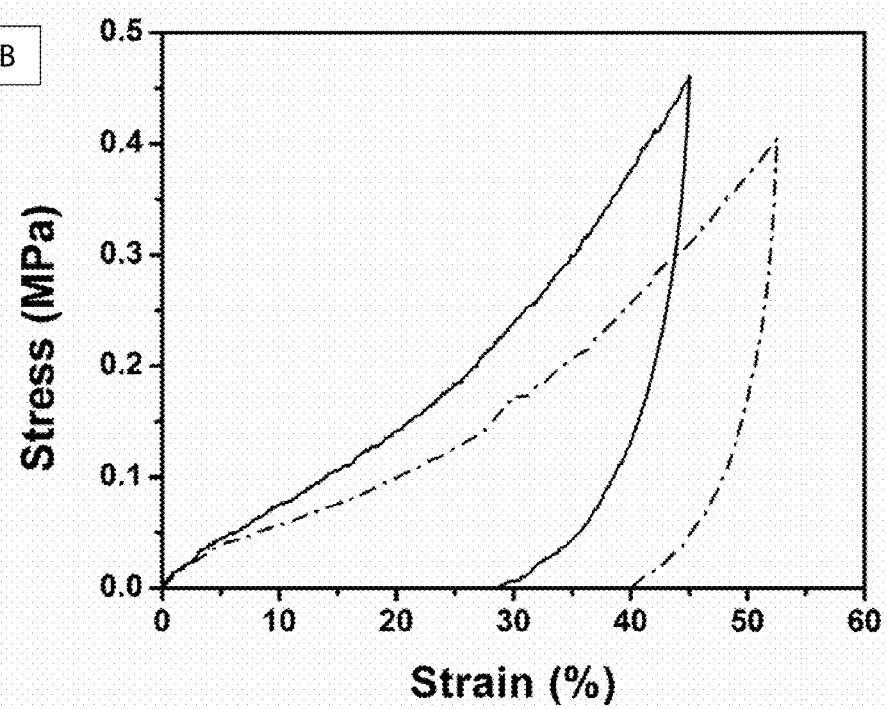
FIG. 8B is a graph of compressive response of the virgin MiGel (i) and healed MiGel (iii) from FIG. 8A.

The reversibility of the crosslinks that form the MiGel networks can enable spontaneous healing of the network after it has been disrupted. As shown in FIG. 8A, the MiGels were able to self-adhere after they were severed into two separate fragments. Particularly, FIG. 8A is a picture of (i) virgin 10% w/v MiGel; (ii) the MiGel after severing into two pieces; (iii) the repaired MiGel about 1 minute after the two pieces were put back together. Inter- or intra-micellar bonds were quickly (about 1 minute) re-established when the surface of the two fragments were brought into close contact with one another. The reformed network exhibited similar mechanical properties as the native MiGel before disruption (FIG. 8B, showing compressive stress response of the virgin (solid) and healed (dashed) 10% w/v MiGel). The MiGel self-healing process had a time scale on the order of few minutes, which was faster than many other self-healing hydrogels[61] and thus can enable rapid MiGel self-repair in applications involving fast mechanical disturbances.

CONCLUSIONS

Disclosed herein is a novel type of hierarchical, reversibly crosslinked hydrogel that comprises ELP micelles that display a high density of a metal coordination peptide motif on the surface. Upon addition of Zn$^{2+}$, the micelles crosslink into stiff hydrogels with high porosity. The network is formed and held together through the crosslinking of the micelle surfaces via metal coordination bonds and by van der Waals and hydrophobic interactions in the cores of the micelles. The gels have higher storage modulus and compressive modulus compared to other similar bio-based, non-covalently crosslinked hydrogels. The gels dissipate energy readily under compressive loading and exhibit self-healing after network disruption due to the reversible nature of the crosslinks comprising the network. The novel MiGels have potential for use in a wide range of applications, including those in which biocompatibility, bio-stability, and high mechanical strength are needed in a single gel.

REFERENCES (1) Lewis, A. L.; Gonzalez, M. V.; Lloyd, A. W.; Hall, B.; Tang, Y.; Willis, S. L.; Leppard, S. W.; Wolfenden, L. C.; Palmer, R. R.; Stratford, P. W. *Journal of vascular and interventional radiology* 2006, 17, 335.

(2) Bruix, J.; Sherman, M. *Hepatology* 2005, 42, 1208.

(3) Lammer, J.; Malagari, K.; Vogl, T.; Pilleul, F.; Denys, A.; Watkinson, A.; Pitton, M.; Sergent, G.; Pfammatter, T.; Terraz, S.; Benhamou, Y.; Avajon, Y.; Gruenberger, T.; Pomoni, M.; Langenberger, H.; Schuchmann, M.; Dumortier, J.; Mueller, C.; Chevallier, P.; Lencioni, R.; On Behalf of the, P. V. I. *Cardiovascular and Interventional Radiology* 2010, 33, 41.

(4) Varela, M.; Real, M. I.; Burrel, M.; Forner, A.; Sala, M.; Brunet, M.; Ayuso, C.; Castells, L.; Montañá, X.; Llovet, J. M.; Bruix, J. *Journal of Hepatology* 2007, 46, 474.

(5) Calogero, C.; Filippo, S.; Ambrogio, O.; Maddalena, A.; Lillian, S.; Franco, T.; Pietro, A.; Antonio, C.; Mario, C. *Radiology* 2002, 224, 47.

(6) Namur, J.; Wassef, M.; Millot, J.-M.; Lewis, A. L.; Manfait, M.; Laurent, A. *Journal of Vascular and Interventional Radiology* 2010, 21, 259.

(7) MacKay, J. A.; Chen, M. N.; McDaniel, J. R.; Liu, W. G.; Simnick, A. J.; Chilkoti, A. *Nature materials* 2009, 8, 993.

(8) Yamada, R.; Sato, M.; Kawabata, M.; Nakatsuka, H.; Nakamura, K.; Takashima, S. *Radiology* 1983, 148, 397.

(9) Joscelyne, S. M.; Trägårdh, G. *Journal of Membrane Science* 2000, 169, 107.

(10) a) E. F. Banwell, E. S. Abelardo, D. J. Adams, M. A. Birchall, A. Corrigan, A. M. Donald, M. Kirkland, L. C. Serpell, M. F. Butler, D. N. Woolfson, *Nat. Mat.* 2009, 8, 596; b) O. D. Krishna, K. L. Kiick, *Biopolymers* 2010, 94, 32; c) L. A. Reis, L. L. Y. Chiu, Y. Liang, K. Hyunh, A. Momen, M. Radisic, *Acta Biomater.* 2012, 8, 1022; d) A. Skerra, *J. Mol. Recognit.* 2000, 13, 167; e) C. G. Tate, G. F. X. Schertler, *Curr. Opin. Struct. Biol.* 2009, 19, 386.

(11) N. Chennamsetty, V. Voynov, V. Kayser, B. Helk, B. L. Trout, *Proc. Natl. Acad. Sci. U.S.A.* 2009, 106, 11937.

(12) B. V. Slaughter, S. S. Khurshid, O. Z. Fisher, A. Khademhosseini, N. A. Peppas, *Adv. Mater.* 2009, 21, 3307.

(13) J. R. Luther, C. E. Glatz, *Biotechnol. Bioeng.* 1994, 44, 147.

(14) a) R. Capone, S. Blake, M. R. Restrepo, J. Yang, M. Mayer, *J. Am. Chem. Soc.* 2007, 129, 9737; b) A. Hennig, G. J. Gabriel, G. N. Tew, S. Matile, *J. Am. Chem. Soc.* 2008, 130, 10338.

(15) S. Banta, I. R. Wheeldon, M. Blenner *Annu. Rev. Biomed. Eng.* 2010 12, 167

(16) C. Foo, J. S. Lee, W. Mulyasasmita, A. Parisi-Amon, S. C. Heilshorn, *Proc. Natl. Acad. Sci. U.S.A* 2009, 106, 22067.

(17) W. E. Hennink, C. F. van Nostrum, *Adv. Drug Del. Rev.* 2012, 64, 223.

(18) a) J. Berger, M. Reist, J. M. Mayer, O. Felt, N. A. Peppas, R. Gurny, *Eur. J. Pharm. Biopharm.* 2004, 57, 19; b) G. D. Nicodemus, S. J. Bryant, *Tissue Engineering Part B-Reviews* 2008, 14, 149.

(19) W. E. Hennink, C. F. van Nostrum, *Adv. Drug Del. Rev.* 2002, 54, 13.

(20) a) J. A. Gustafson, R. A. Price, J. Frandsen, C. R. Henak, J. Cappello, H. Ghandehari, *Biomacromolecules* 2013, 14, 618; b) M. J. Reilly, *Colloids Surf. B*, 2008, 63, 2, 269.

[21] J. Y. Sun, X. H. Zhao, W. R. K. Illeperuma, O. Chaudhuri, K. H. Oh, D. J. Mooney, J. J. Vlassak, Z. G. Suo, *Nature* 2012, 489, 133.

[22] a) W. C. Lin, W. Fan, A. Marcellan, D. Hourdet, C. Creton, *Macromolecules* 2010, 43, 2554; b) S. K. Agrawal, N. Sanabria-DeLong, G. N. Tew, S. R. Bhatia, *Langmuir* 2008, 24, 13148.

[23] D. C. Tuncaboylu, M. Sari, W. Oppermann, O. Okay, *Macromolecules* 2011, 44, 4997.

[24] J. Brassinne, A. M. Stevens, E. Van Ruymbeke, J. F. Gohy, C. A. Fustin, *Macromolecules* 2013, 46, 9134.

[25] M. J. Glassman, B. D. Olsen, *Soft Matter* 2013, 9, 6814.

[26] a) B. S. Kim, S. W. Park, P. T. Hammond, *Acs Nano* 2008, 2, 386; b) A. Laschewsky, P. Muller-Buschbaum, C. M. Papadakis Intelligent Hydrogels, Vol. 140 Eds.: G. Sadowski and W. Richtering, 2013, 15.

[27] a) L. Wei, C. H. Cai, J. P. Lin, T. Chen, *Biomaterials* 2009, 30, 2606; b) D. Ma, H. B. Zhang, K. Tu, L. M. Zhang, *Soft Matter* 2012, 8, 3665.

[28] a) P. Guillet, C. Mugemana, F. J. Stadler, U. S. Schubert, C. A. Fustin, C. Bailly, J. F. Gohy, *Soft Matter* 2009, 5, 3409; b) L. X. Xiao, J. H. Zhu, J. D. Londono, D. J. Pochan, X. Q. Jia, *Soft Matter* 2012, 8, 10233.

[29] B. D. Olsen, J. A. Kornfield, D. A. Tirrell, *Macromolecules* 2010, 43, 9094.

[30] J. D. Hartgerink, E. Beniash, S. I. Stupp, *Science* 2001, 294, 1684.

[31] E. R. Wright, V. P. Conticello, R. P. Apkarian, *Microsc. Microanal.* 2003, 9, 171.

[32] M. A. Meyers, P. Y. Chen, A. Y. M. Lin, Y. Seki, *Prog. Mater Sci.* 2008, 53, 1.

[33] S. Bechtle, S. F. Ang, G. A. Schneider, *Biomaterials* 2010, 31, 6378.

[34] M. Vanderrest, R. Garrone, *FASEB J.* 1991, 5, 2814.

[35] a) A. J. Maniotis, C. S. Chen, D. E. Ingber, *Proc. Natl. Acad. Sci. U.S.A* 1997, 94, 849; b) A. McGough, B. Pope, W. Chiu, A. Weeds, *J. Cell Biol.* 1997, 138, 771.

[36] N. Mizuno, A. Narita, T. Kon, K. Sutoh, M. Kikkawa, *Proc. Natl. Acad. Sci. U.S.A* 2007, 104, 20832.

[37] a) I. Massova, L. P. Kotra, R. Fridman, S. Mobashery, *FASEB J.* 1998, 12, 1075; b) F. Loechel, U. M. Wewer, *FEBS Lett.* 2001, 506, 65.

[38] J. H. Waite, X.-X. Qin, K. J. Coyne, *Matrix Biol.* 1998, 17, 93.

[39] D. E. Meyer, A. Chilkoti, *Biomacromolecules* 2004, 5, 846.

[40] A. Ghoorchian, N. B. Holland, *Biomacromolecules* 2011, 12, 4022.

[41] D. W. Urry, T. L. Trapane, K. U. Prasad, *Biopolymers* 1985, 24, 2345.

[42] a) D. E. Meyer, A. Chilkoti, *Biomacromolecules* 2002, 3, 357; b) Y. H. Cho, Y. J. Zhang, T. Christensen, L. B. Sagle, A. Chilkoti, P. S. Cremer, *J. Phys. Chem. B* 2008, 112, 13765.

[43] a) D. E. Meyer, A. Chilkoti, *Nat. Biotechnol.* 1999, 17, 1112; b) D. T. McPherson, C. Morrow, D. S. Minehan, J. G. Wu, E. Hunter, D. W. Urry, *Biotechnol. Prog.* 1992, 8, 347.

[44] a) M. R. Dreher, A. J. Simnick, K. Fischer, R. J. Smith, A. Patel, M. Schmidt, A. Chilkoti, *J. Am. Chem. Soc.* 2008, 130, 687; b) J. R. McDaniel, S. R. MacEwan, X. H. Li, D. C. Radford, C. D. Landon, M. Dewhirst, A. Chilkoti, *Nano Lett.* 2014, 14, 2890; c) D. J. Callahan, W.

E. Liu, X. H. Li, M. R. Dreher, W. Hassouneh, M. Kim, P. Marszalek, A. Chilkoti, *Nano Lett.* 2012, 12, 2165; d) A. J. Simnick, M. Amiram, W. G. Liu, G. Hanna, M. W. Dewhirst, C. D. Kontos, A. Chilkoti, *J. Controlled Release* 2011, 155, 144; e) W. Hassouneh, K. Fischer, S. R. MacEwan, R. Branscheid, C. L. Fu, R. H. Liu, M. Schmidt, A. Chilkoti, *Biomacromolecules* 2012, 13, 1598.

[45] E. Hadler-Olsen, B. Fadnes, I. Sylte, L. Uhlin-Hansen, J. O. Winberg, *FEBS J.* 2011, 278, 28.

[46] W. Bode, F. X. Gomisruth, W. Stockier, *FEBS Lett.* 1993, 331, 134.

[47] K. Kasperek, L. E. Feinendegen, I. Lombeck, H. J. Bremer, *Eur. J. Pediatr.* 1977, 126, 199.

[48] P. Trumbo, A. A. Yates, S. Schlicker, M. Poos, *J. Am. Diet. Assoc.* 2001, 101, 294.

[49] a) J. Danielsson, J. Jarvet, P. Damberg, A. Graslund, *Magn. Reson. Chem.* 2002, 40, S89; b) A. Ghoorchian, K. Vandemark, K. Freeman, S. Kambow, N. B. Holland, K. A. Streletzky, *J. Phys. Chem. B* 2013, 117, 8865; c) A. Ghoorchian, J. T. Cole, N. B. Holland, *Macromolecules* 2010, 43, 4340.

[50] J. R. McDaniel, J. Bhattacharyya, K. B. Vargo, W. Hassouneh, D. A. Hammer, A. Chilkoti, *Angewandte Chemie-International Edition* 2013, 52, 1683.

[51] W. Brown, *Dynamic Light Scattering: The Method And Some Applications*, Clarendon Press, 1993, p.

[52] H. Kumari, S. R. Kline, J. L. Atwood, *Chemical Science* 2014, 5, 2554.

[53] B. Bharti, J. Meissner, G. H. Findenegg, *Langmuir* 2011, 27, 9823.

[54] J. S. Pedersen, C. Svaneborg, K. Almdal, I. W. Hamley, R. N. Young, *Macromolecules* 2003, 36, 416.

[55] S. Chandrasekhar, *Reviews of Modern Physics* 1943, 15, 0001.

[56] a) K. J. Jeong, A. Panitch, *Biomacromolecules* 2009, 10, 1090; b) C. Q. Yan, D. J. Pochan, *Chem. Soc. Rev.* 2010, 39, 3528; c) J. T. Cirulis, F. W. Keeley, D. F. James, *J. Rheol.* 2009, 53, 1215; d) D. Asai, D. H. Xu, W. G. Liu, F. G. Quiroz, D. J. Callahan, M. R. Zalutsky, S. L. Craig, A. Chilkoti, *Biomaterials* 2012, 33, 5451; e) D. H. Xu, D. Asai, A. Chilkoti, S. L. Craig, *Biomacromolecules* 2012, 13, 2315; f) D. G. Abebe, T. Fujiwara, *Biomacromolecules* 2012, 13, 1828; g) V. Breedveld, A. P. Nowak, J. Sato, T. J. Deming, D. J. Pine, *Macromolecules* 2004, 37, 3943.

[57] T. Saito, T. Uematsu, S. Kimura, T. Enomae, A. Isogai, *Soft Matter* 2011, 7, 8804.

[58] C. R. Rubinstein M, *Polymer Physics*, Oxford University Press, 2012, p.

[59] L. H. Beun, I. M. Storm, M. W. T. Werten, F. A. de Wolf, M. A. C. Stuart, R. de Vries, *Biomacromolecules* 2014, 15, 3349.

[60] a) D. G. Barrett, D. E. Fullenkamp, L. H. He, N. Holten-Andersen, K. Y. C. Lee, P. B. Messersmith, *Adv. Fund. Mater.* 2013, 23, 1111; b) D. E. Fullenkamp, L. He, D. G. Barrett, W. R. Burghardt, P. B. Messersmith, *Macromolecules* 2013, 46, 1167.

[61] a) M. Guvendiren, H. D. Lu, J. A. Burdick, *Soft Matter* 2012, 8, 260; b) N. Holten-Andersen, M. J. Harrington, H. Birkedal, B. P. Lee, P. B. Messersmith, K. Y. C. Lee, J. H. Waite, *Proc. Natl. Acad. Sci. U.S.A* 2011, 108, 2651; c) M. Nakahata, Y. Takashima, H. Yamaguchi, A. Harada, *Nature Communications* 2011, 2; d) M. M. C. Bastings, S. Koudstaal, R. E. Kieltyka, Y. Nakano, A. C. H. Pape, D. A. M. Feyen, F. J. van Slochteren, P. A. Doevendans, J. P. G. Sluijter, E. W. Meijer, S. A. J. Chamuleau, P. Y. W. Dankers, *Adv. Healthcare Mat.* 2014, 3, 70.

[62] J. R. McDaniel, J. A. MacKay, F. G. Quiroz, A. Chilkoti, *Biomacromolecules* 2010, 11, 944.

[63] W. Hassouneh, S. R. MacEwan, A. Chilkoti, *Methods in Enzymology*, Vol. 502 Eds.: K. D. Wittrup and G. L. Verdine, 2012, 215.

[64] Meyer, D. E.; Chilkoti, A. *Nat Biotech* 1999, 17, 1112.

[65] Chung, C.; Lampe, K. J.; Heilshorn, S. C. *Biomacromolecules* 2012, 13, 3912.

[66] McDaniel, J. R.; Bhattacharyya, J.; Vargo, K. B.; Hassouneh, W.; Hammer, D. A.; Chilkoti, A. *Angewandte Chemie (International ed. in English)* 2013, 52, 1683.

What is claimed is:

1. A hydrogel comprised of reversibly crosslinked micelles, the hydrogel comprising:
   a. a plurality of a peptide polymer consisting essentially of a hydrophobic portion of 40 to 80 repeats of a VPGVG (SEQ ID NO: 1) peptide motif, a hydrophilic portion of 10 to 50 repeats of a VPGAGVPGGG (SEQ ID NO: 2) peptide motif, and a separate peptide metal binding sequence at a terminus of the hydrophilic portion, wherein the peptide polymer is in the form of a plurality of micelles having the hydrophobic portion at a core of the micelles and the metal binding sequence at a surface of the micelles; and
   b. a plurality of metal ions bound at the metal binding sequences, wherein the plurality of micelles are reversibly crosslinked through the bound metal ions.

2. The hydrogel of claim 1, wherein the peptide metal binding sequence comprises a motif HEDGHWDGSEHGY (SEQ ID NO: 3) and the metal comprises one or more of transition metals $Zn^{2+}$, $Ni^{2+}$, or $Cu^{2+}$.

3. The hydrogel of claim 2, wherein the metal is $Zn^{2+}$.

4. The hydrogel of claim 1, wherein the peptide polymer further comprises a hydrophobic therapeutic agent attached to the hydrophobic portion at the core of the micelles.

5. The hydrogel of claim 4, wherein the hydrophobic therapeutic agent is attached to the hydrophobic portion through a linker, and wherein the linker includes an enzymatic cleavage site to allow for release of the hydrophobic therapeutic agent from the micelle.

6. The hydrogel of claim 4, wherein the hydrophobic therapeutic agent is attached to the hydrophilic portion through a linker, and wherein the linker includes a pH sensitive cleavage site to allow for release of the hydrophobic therapeutic agent from the micelle.

7. The hydrogel of claim 1, further comprising an interpenetrating mesh consisting essentially of covalently crosslinked polymers, wherein the mesh surrounds the reversibly crosslinked micelles without being covalently attached to the micelles.

8. The hydrogel of claim 7, wherein the covalently crosslinked polymers comprise polypeptides, elastin-like polypeptides (ELP), biopolymers, synthetic polymers, or branched polymers, and combinations thereof.

9. A method of making a hydrogel comprised of reversibly crosslinked micelles, the method comprising:
heating a plurality of a peptide polymer consisting essentially of a hydrophobic portion of 40 to 80 repeats of a VPGVG (SEQ ID NO: 1) peptide motif, a hydrophilic portion of 10 to 50 repeats of a VPGAGVPGGG (SEQ ID NO: 2) peptide motif, and a separate peptide metal binding sequence at near a terminus of the hydrophilic portion, wherein the peptide polymer takes the form of a plurality of micelles having the hydrophobic portion at a core of the micelles and the metal binding sequences at a surface of the micelles; and
adding a plurality of metal ions to the micelles, wherein the plurality of micelles are reversibly crosslinked through the bound metal ions at the metal binding sequences.

10. The method of claim 9, wherein the peptide polymer further comprises a hydrophobic therapeutic agent attached to the hydrophobic portion, wherein the hydrophobic therapeutic agent is at the core of the micelles along with the hydrophobic portion.

11. The method of claim 9, further comprising adding a plurality of a polymer and a crosslinking agent, wherein the plurality of polymers are covalently crosslinked to each other to form an interpenetrating mesh consisting essentially of the covalently crosslinked polymers, wherein the interpenetrating mesh surrounds the reversibly crosslinked micelles without being covalently attached to the micelles.

12. A hydrogel loaded with a therapeutic molecule, the hydrogel comprising:
a. a plurality of a peptide polymer consisting essentially of a hydrophilic portion of 60 to 100 repeats of a VPGAG (SEQ ID NO: 6) peptide motif and a separate peptide metal binding sequence at a terminus of the hydrophilic portion; and having a hydrophobic therapeutic agent attached near an opposing terminus of the hydrophilic portion, wherein the peptide polymer is in the form of a plurality of micelles having the hydrophobic therapeutic agent at a core of the micelles and the metal binding sequences at a surface of the micelles; and
b. a plurality of metal ions bound at the metal binding sequences, wherein the plurality of micelles are reversibly crosslinked through the bound metal ions.

13. The hydrogel of claim 12, wherein the peptide metal binding site comprises a motif HEDGHWDGSEHGY (SEQ ID NO: 3) and the metal comprises one or more of transition metals Zn2+, Ni2+, or Cu2+.

14. The hydrogel of claim 13, wherein the metal is Zn2+.

15. The hydrogel of claim 12, wherein the hydrophobic therapeutic agent is attached to the hydrophilic portion through a linker, and wherein the linker includes an enzymatic cleavage site to allow for release of the hydrophobic therapeutic agent from the micelle.

16. The hydrogel of claim 12, wherein the hydrophobic therapeutic agent is attached to the hydrophilic portion through a linker, and wherein the linker includes a pH sensitive cleavage site to allow for release of the hydrophobic therapeutic agent from the micelle.

17. The hydrogel of claim 12, further comprising an interpenetrating mesh consisting essentially of covalently crosslinked polymers, wherein the mesh surrounds the reversibly crosslinked micelles without being covalently attached to the micelles.

18. The hydrogel of claim 17, wherein the covalently crosslinked polymers comprise polypeptides, elastin-like polypeptides (ELP), biopolymers, synthetic polymers, or branched polymers, and combinations thereof.

19. A method of making a hydrogel loaded with a therapeutic agent, the method comprising:
attaching a hydrophobic therapeutic agent at a terminus of a plurality of a peptide polymer consisting essentially of 60 to 100 repeats of a VPGAG (SEQ ID NO: 6) peptide motif and a separate peptide metal binding sequence at an opposing terminus, wherein the peptide polymer takes the form of a plurality of micelles having the attached hydrophobic therapeutic agent a core of the micelles and the metal binding sequences at a surface of the micelles; and
adding a plurality of metal ions to the micelles, wherein the plurality of micelles are reversibly crosslinked through the bound metal ions at the metal binding sequences.

20. The method of claim 19, further comprising adding a plurality of a polymer and a crosslinking agent, wherein the plurality of polymers are covalently crosslinked to each other to form an interpenetrating mesh consisting essentially of the covalently crosslinked polymers, wherein the interpenetrating mesh surrounds the reversibly crosslinked micelles without being covalently attached to the micelles.

* * * * *